United States Patent
Meyer

(10) Patent No.: US 11,684,647 B2
(45) Date of Patent: *Jun. 27, 2023

(54) METHODS, COMPOSITIONS, AND KITS ADDRESSING DEPRESSED MOOD

(71) Applicant: Centre for Addiction and Mental Health, Toronto (CA)

(72) Inventor: Jeffrey H. Meyer, Toronto (CA)

(73) Assignee: CENTRE FOR ADDICTION AND MENTAL HEALTH, Toronto (CA)

( * ) Notice: Subject to any disclaimer, the term of this patent is extended or adjusted under 35 U.S.C. 154(b) by 288 days.

This patent is subject to a terminal disclaimer.

(21) Appl. No.: 17/091,128

(22) Filed: Nov. 6, 2020

(65) Prior Publication Data

US 2021/0052684 A1 Feb. 25, 2021

Related U.S. Application Data

(60) Continuation-in-part of application No. 16/655,746, filed on Oct. 17, 2019, now Pat. No. 10,828,343, which is a division of application No. 16/019,039, filed on Jun. 26, 2018, now Pat. No. 10,478,467, which is a continuation-in-part of application No. 15/318,465, filed as application No. PCT/CA2015/050548 on Jun. 12, 2015, now Pat. No. 10,034,852.

(60) Provisional application No. 62/011,888, filed on Jun. 13, 2014.

(51) Int. Cl.
| | |
|---|---|
| A61K 36/45 | (2006.01) |
| A61K 31/405 | (2006.01) |
| A61K 36/315 | (2006.01) |
| A61K 31/352 | (2006.01) |
| A61K 31/197 | (2006.01) |
| A61P 25/24 | (2006.01) |

(52) U.S. Cl.
CPC ............ *A61K 36/45* (2013.01); *A61K 31/197* (2013.01); *A61K 31/352* (2013.01); *A61K 31/405* (2013.01); *A61K 36/315* (2013.01); *A61P 25/24* (2018.01)

(58) Field of Classification Search
CPC .................................................. A61K 36/45
See application file for complete search history.

(56) References Cited

U.S. PATENT DOCUMENTS

| | | | | |
|---|---|---|---|---|
| 4,377,595 A | 3/1983 | Wurtman | | |
| 6,083,526 A | 7/2000 | Gorbach | | |
| 10,034,852 B2 * | 7/2018 | Meyer | ................. | A61K 31/355 |
| 10,478,467 B2 * | 11/2019 | Meyer | ................. | A61K 31/197 |
| 10,828,343 B2 * | 11/2020 | Meyer | ..................... | A61P 25/24 |
| 2007/0286909 A1 | 12/2007 | Smith et al. | | |

OTHER PUBLICATIONS

Clark., "The Velten Mood Induction Procedure and Cognitive Models of Depression: A Reply to Riskind and Rholes (1985)," Behaviour Research and Therapy, 1985, vol. 23 (6), pp. 667-669.
Dornbos et al., "Sequential Serotonin and Noradrenalin Associated Processes Involved in Postpartum Blues," Progress in Neuro-Psychopharmacology & Biological Psychiatry, Jul. 2008, vol. 32 (5), pp. 1320-1325.
Dowalti et al., "Novel Strategy for Preventing Postpartum Depression," Annals of Nutrition and Metabolism, 2013, vol. 63 (1), Abstract No. P0081, pp. 296.
Dowalti et al., "P.1.g.078 Approaches to Create Dietary Supplements to Prevent Postpartum Depression," European Neuropsychopharmacology, Oct. 2013, vol. 23 (2), pp. S235-S236.
Dowlati., et al., "Effect of Dysfunctional Attitudes and Postpartum State on Vulnerability to Depressed Mood," Journal of Affective Disorders, Mar. 2014, vol. 161, pp. 16-20.
European Patent Application No. 15806621.7, Extended European Search Report dated Dec. 7, 2017.
European Patent Application No. 15806621.7, Office Action dated Mar. 17, 2020.
Gautam, "Role of Antioxidants in Generalized Anxiety Disorder and Depression," Indian Journal of Psychiatry, Jul.-Sep. 2012, vol. 54 (3), pp. 244-247.
Haytowitz., et al., "USDA Database for the Oxygen Radical Absorbance Capacity (ORAC) of Selected Foods, Release 2," May 2010, pp. 1-46.
International Patent Application No. PCT/CA2015/050548, International Preliminary Report on Patentability dated Dec. 22, 2016.
International Patent Application No. PCT/CA2015/050548, International Search Report and Written Opinion dated Oct. 2, 2015.
ION Archives (Institute for Optimum Nutrition), Depression, [online], Winter 1998. Retrieved from the Internet: URL: http://www.ion.ac.uk/information/onarchives/depression.
Krikorian et al., "Blueberry Supplementation Improves Memory in Older Adults," Journal of Agricultural and Food Chemistry, Apr. 2010, vol. 58 (7), pp. 3996-4000.
Kurth et al., "Predictors of Crying Problems in the Early Postpartum Period," Journal of Obstetric, Gynecologic, and Neonatal Nursing, 2010, vol. 39 (3), pp. 250-262.
Meyer et al., "Brain Monoamine Oxidase a Binding in Major Depressive Disorder," Archives of General Psychiatry, Dec. 2009, vol. 66 (12), pp. 1304-1312.

(Continued)

*Primary Examiner* — Nizal S Chandrakumar
(74) *Attorney, Agent, or Firm* — Borden Ladner Gervais LLP; Kathleen E. Marsman

(57) ABSTRACT

A method of treating or preventing postpartum blues or depression is described, comprising administering to a subject in need thereof: an antioxidant source; a tryptophan composition comprising from 1.0 g to 5.0 g of tryptophan; and a tyrosine composition comprising from 2.0 g to 50 g of tyrosine. The antioxidant source may comprise a food or an extract derived from such a food as grapes, berries such as blueberries, citrus fruit, pomegranate, tomato, squash, carrot, sweet potato, dark green vegetables, beets, leafy vegetables, *Brassica oleracea* vegetables, peppers, melons, pineapples, lentils, plant oils, and/or tree nuts.

25 Claims, 8 Drawing Sheets

(56) References Cited

OTHER PUBLICATIONS

Meyer et al., "Elevated Monoamine Oxidase A levels in the Brain," Archives of General Psychiatry, Nov. 2006, vol. 63, pp. 1209-1216.

Michel et al., "The Role of Oxidative Stress in Depressive Disorders," Current Pharmaceutical Design, 2012, vol. 18 (36), pp. 5890-5899.

Ohara., et al., "Prospective Study of Postpartum Blues Biologic and Psychosocial Factors," Archives General Psychiatry, Sep. 1991, vol. 48, pp. 801-806.

Ohara., et al., "Rates and Risk of Postpartum Depression a Meta-Analysis," International Review of Psychiatry, 1996, vol. 8, pp. 37-54.

Praschak-Rieder et al., "Effects of Tryptophan Depletion on the Serotonin Transporter in Healthy Humans," Biological Psychiatry, Nov. 2005, vol. 58 (10), pp. 825-830.

Prior., et al., "Assays for Hydrophilic and Lipophilic Antioxidant Capacity (oxygen radical absorbance capacity (ORACFL)) of Plasma and Other Biological and Food Samples," Journal of Agricultural and Food Chemistry, May 2003, vol. 51 (11), pp. 3273-3279.

Rekkas., et al., "Greater Monoamine Oxidase A Binding in Peri menopausal Age as Measured With Carbon 11-Labeled Harmine Positron Emission Tomography," JAMA Psychiatry, Aug. 2014, vol. 71 (8), pp. E1-E7.

Riskind, "The Velten Mood Induction Procedure and Cognitive Manipulation: Our Response to Clark," Behaviour Research and Therapy, Jan. 1985, vol. 23 (6), pp. 671-673.

Sacher et al., "Elevated Brain Monoamine Oxidase a Binding in the Early Postpartum Period," Archives of General Psychiatry, May 2010, vol. 67 (5), pp. 468-474.

Sacher et al., "Relationship of Monoamine Oxidase—A Distribution Volume to Postpartum Depression and Postpartum Crying," Neuropsychopharmacology, Jan. 2015, vol. 40 (2), pp. 429-435.

Smith., et al., "Effects of Ovarian Steroids and Raloxifene on Proteins that Synthesize, Transport, and Degrade Serotonin in the Raphe Region of Macaques," Neuropsychopharmacology, Nov. 2004, vol. 29 (11), pp. 2035-2045.

Sullivan, "Tryptophan, Tyrosine May Battle Early Postpartum Depression," Clinical Psychiatry News, Mar. 18, 2011.

U.S. Appl. No. 16/655,746, Notice of Allowance dated Jul. 1, 2020.

U.S. Appl. No. 15/318,465, Non-Final Office Action dated Oct. 12, 2017.

U.S. Appl. No. 15/318,465, Notice of Allowance dated Mar. 28, 2018.

U.S. Appl. No. 15/318,465, Restriction Requirement dated May 22, 2017.

U.S. Appl. No. 16/019,039, Non-Final Office Action dated Mar. 11, 2019.

U.S. Appl. No. 16/019,039, Notice of Allowance dated Jul. 17, 2019.

U.S. Appl. No. 16/019,039, Restriction Requirement dated Nov. 5, 2018.

U.S. Appl. No. 16/655,746, Notice of Allowance dated Aug. 18, 2020.

Velten., "A Laboratory Task for Induction of Mood States," Behaviour Research and Therapy, 1968, vol. 6, pp. 473-482.

Wu et al., "Concentrations of Anthocyanins in Common Foods in the United States and Estimation of Normal Consumption," Journal of Agricultural and Food Chemistry, May 2006, vol. 54 (11), pp. 4069-4075.

Xu et al., "Novel Therapeutic Targets in Depression and Anxiety: Antioxidants as a Candidate Treatment," Current Neuropharmacology, Mar. 2014, vol. 12 (2), pp. 108-119.

Canadian Patent Application No. 2,951,955, Office Action dated Jul. 23, 2021.

European Patent Application No. 21186364.2, Extended European Search Report dated Nov. 3, 2021.

* cited by examiner

METHODS, COMPOSITIONS, AND KITS ADDRESSING DEPRESSED MOOD

CROSS REFERENCE TO RELATED APPLICATIONS

This application is a Continuation-In-Part of and claims the benefit of priority of U.S. patent application Ser. No. 16/655,746 filed Oct. 17, 2019; which is a Divisional of and claims the benefit of priority of U.S. patent application Ser. No. 16/019,039 filed Jun. 26, 2018; which is a Continuation-In-Part of and claims the benefit of priority of U.S. patent application Ser. No. 15/318,465 filed Dec. 13, 2016; which is the National Phase of and claims the benefit of priority of International PCT Application No. CA2015/050548 filed Jun. 12, 2015; which claims the benefit of priority of U.S. Provisional Patent Application No. 62/011,888 filed Jun. 13, 2014, The above-noted patent application U.S. Ser. No. 16/655,746; U.S. Ser. No. 16/019,039; U.S. Ser. No. 15/318,465; PCT/CA2015/050548; and U.S. 62/011,888 are hereby incorporated by reference herein.

FIELD

The present disclosure relates generally to methods, compositions, kits, and uses thereof to address depressed mood, for example by treatment, amelioration, or prevention of depressed mood.

BACKGROUND

The early postpartum period, specifically the first few weeks after delivery, is a time of high risk for a major depressive episode, also referred to as postpartum depression. During this time there is a heightened vulnerability for low mood due to postpartum blues. Severe postpartum blues may indicate the onset of postpartum depression (O'Hara et al., 1991). The sadness commonly observed around day-5 postpartum is considered in the healthy range of experience. However, it has also been observed that vulnerability to depressed mood is highly correlated to postpartum blues at day-5 and to exhibition of dysfunctional attitudes on day-5 postpartum (Dowlati et al, 2014). The neurobiological mechanisms leading to postpartum blues and postpartum depression are unclear.

Monoamine oxidase A (MAO-A) is a pro oxidant enzyme with the ability to metabolize monoamines such as serotonin, norepinephrine, and dopamine which help to maintain normal mood. Serotonin, norepinephrine, and dopamine levels are observed to be lowered during major depressive episodes. Elevated MAO-A levels are observed in individuals with major depressive disorder during a major depressive episode, and may contribute to monoamine-lowering observed during a major depressive episode in depressed individuals (Meyer et al., 2006; and Meyer et al., 2009).

Following delivery, estrogen levels typically drop 100- to 1000-fold during the first 3 to 4 days postpartum (O'Hara et al, 1996). Changes in estrogen levels have an inverse relationship with MAO-A levels (smith et al, 2004). Elevated MAO-A levels in early postpartum can serve as a marker of a monoamine-lowering process that contributes to mood changes associated with postpartum blues (Sacher et al., 2010).

Antidepressant medication can be utilized to address postpartum blues and postpartum depression. However, drug utilization carries with it concerns about side effects, and potential drug excretion into breast milk.

U.S. Pat. No. 6,083,526 (Gorach) suggests the use of a composition containing purified isoflavonoids, for example as derived from soy, for treating or preventing postpartum depression. The treatment purports to impart effect because of parallels between the chemical structure of isoflavonoids and estrogens, thus imparting an estrogen-like effect by increase of circulating isoflavonoids. No data is provided to illustrate any beneficial effect.

It has been suggested that dietary supplementation of tryptophan and tyrosine may be utilized to address postpartum blues or postpartum depression, as reported by Sullivan 2011, quoting J. H. Meyer at $4^{th}$ World Congress on Women's Mental Health (Madrid). However no regime or illustration of efficacy was provided.

There is a need to address depressed mood arising in the postpartum period as well as depressed mood arising from other conditions associated with MAO-A levels. It is desirable to develop strategies that seek to address depressed mood.

SUMMARY

It is an object of the present disclosure to obviate or mitigate at least one disadvantage of previous approaches to addressing depressed mood, for example in treating, ameliorating or preventing depressed mood associated with MAO-A levels, postpartum blues or postpartum depression.

A method is provided herein for treatment or prophylaxis of depressed mood in a subject with elevated MAO-A levels, comprising administering to a subject in need thereof: an antioxidant source once daily on at least day-1 of a treatment regime of from 3 to 5 days; wherein the antioxidant source comprises an anthocyanin-containing fruit, vegetable, nut, legume, or a juice or extract thereof, and has an ORAC value of at least about 3000 µmol TE/serving; a tryptophan composition on the evening of the penultimate day of the treatment regime, simultaneously or following the antioxidant source, said tryptophan composition comprising from 1.0 g to 5.0 g of L-tryptophan per serving in free amino acid form, and acceptable diluents; and a tyrosine composition on the final day of the treatment regime, administered the day after administering the tryptophan composition, said tyrosine composition comprising from 2.0 g to 50 g of L-tyrosine per serving in free amino acid form, and acceptable diluents.

Further, a method is provided for treatment or prophylaxis of depressed mood in a subject experiencing excessive crying at up to 18-months postpartum, comprising administering to a subject in need thereof: an antioxidant source once daily on at least day-1 of a treatment regime of from 3 to 5 days; wherein the antioxidant source comprises an anthocyanin-containing fruit, vegetable, nut, legume, or a juice or extract thereof, and has an ORAC value of at least about 3000 µmol TE/serving; a tryptophan composition on the evening of the penultimate day of the treatment regime, simultaneously or following the antioxidant source, said tryptophan composition comprising from 1.0 g to 5.0 g of L-tryptophan per serving in free amino acid form, and acceptable diluents; and a tyrosine composition on the final day of the treatment regime, said tyrosine composition comprising from 2.0 g to 50 g of L-tyrosine per serving in free amino acid form, and acceptable diluents.

Notably, in the method described, use of the antioxidant source by the subject can begin before the treatment regime begins, and can extend after the treatment regime.

Kits are described which include the requisite components of the methods and uses, together with instructions for use.

Specifically, there is provided herein a kit for use in treatment or prophylaxis of depressed mood in a subject in need thereof. The kit comprises at least one serving of an antioxidant source for administration on at least day-1 of a treatment regime of from 3 to 5 days. The antioxidant source comprises an anthocyanin-containing fruit, vegetable, nut, legume, or a juice or extract thereof, and has an ORAC value of at least about 3000 μmol TE/serving. The kit also comprises a serving of a tryptophan composition for evening administration simultaneously or following the antioxidant source on the penultimate day of the treatment regime, wherein the tryptophan composition comprises from 1.0 g to 5.0 g of L-tryptophan per serving in free amino acid form, and an acceptable diluent. The kit also comprises a serving of a tyrosine composition for administration on the final day of the treatment regime, wherein the tyrosine composition comprises from 2.0 g to 50 g of L-tyrosine per serving in free amino acid form together with an acceptable diluent. The kit may also include directions for use in treatment or prophylaxis of depressed mood in the subject.

The antioxidant source of the kit may be blueberries, blueberry juice, blueberry extract or a combination thereof. A combination of blueberry juice and blueberry extract may be used as the antioxidant source. The antioxidant source may additionally comprises grapes; berries; citrus fruit; pomegranate; tomato; squash; carrot; sweet potato; a dark green vegetable; a beet; a leafy vegetable; a *Brassica oleracea* vegetable such as cabbage, broccoli, cauliflower, kale, Brussels sprouts, savoy, or Chinese kale; a pepper; a melon; pineapple; lentils; a plant oil; a tree nut; and/or a juice, extract, or isolated antioxidant compound therefrom.

The tryptophan composition may comprise about 2.0 g of L-tryptophan per serving. The tyrosine composition may comprise from 5.0 g to 20.0 g of L-tyrosine per serving, for example, about 10 g of L-tyrosine per serving. The tryptophan composition may provide about 2 g of L-tryptophan per serving in free amino acid form, and the tyrosine composition may provide about 10 g of L-tyrosine per serving in free amino acid form.

Optionally, the antioxidant source may have an ORAC value of at least about 5000 μmol TE/serving. Further, the antioxidant source may be in a multi-component form comprising two or more of a fluid beverage, an extract, a crystal form and a powder form.

The kit may be provided for a 3 day treatment regime, wherein the tryptophan composition is for administration on the evening of day-2 of the treatment regime, and the tyrosine composition is for administration on the morning of day-3 of the treatment regime. As an example, the antioxidant source may be provided in an amount for two or more days of the treatment regime.

The antioxidant source may be provided in amounts of (a) for 1 to 10 days following the treatment regime, such as 1 to 7 days, or 1 to 3 days; and/or (b) for 1 to 10 days, preceding the treatment regime, such as 1 to 7 days, or 1 to 3 days.

The kit may include the tryptophan composition, the tyrosine composition, and/or the antioxidant source in the form of a pill, capsule, tablet, a gel, a concentrate, a syrup, a bar, a cereal, a beverage, a shake, a powder, or a baked product. The subject who may use the kit may have elevated MAO-A levels. For example, the subject may have elevated MAO-A levels and may experience excessive crying. The kit may be intended for a subject who is experiencing excessive crying and is within 18-months postpartum. Further, the kit may be directed to a subject who is postpartum, and in this case, the treatment regime begins between 1 to 5 days postpartum, or may begin any time within 18 months postpartum.

According to an aspect described herein, a method of treating or preventing postpartum blues or depression, as described herein, comprises administering to a subject in need thereof: an antioxidant source; a tryptophan composition comprising from 1.0 g to 5.0 g of tryptophan; and a tyrosine composition comprising from 2.0 g to 50 g of tyrosine.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
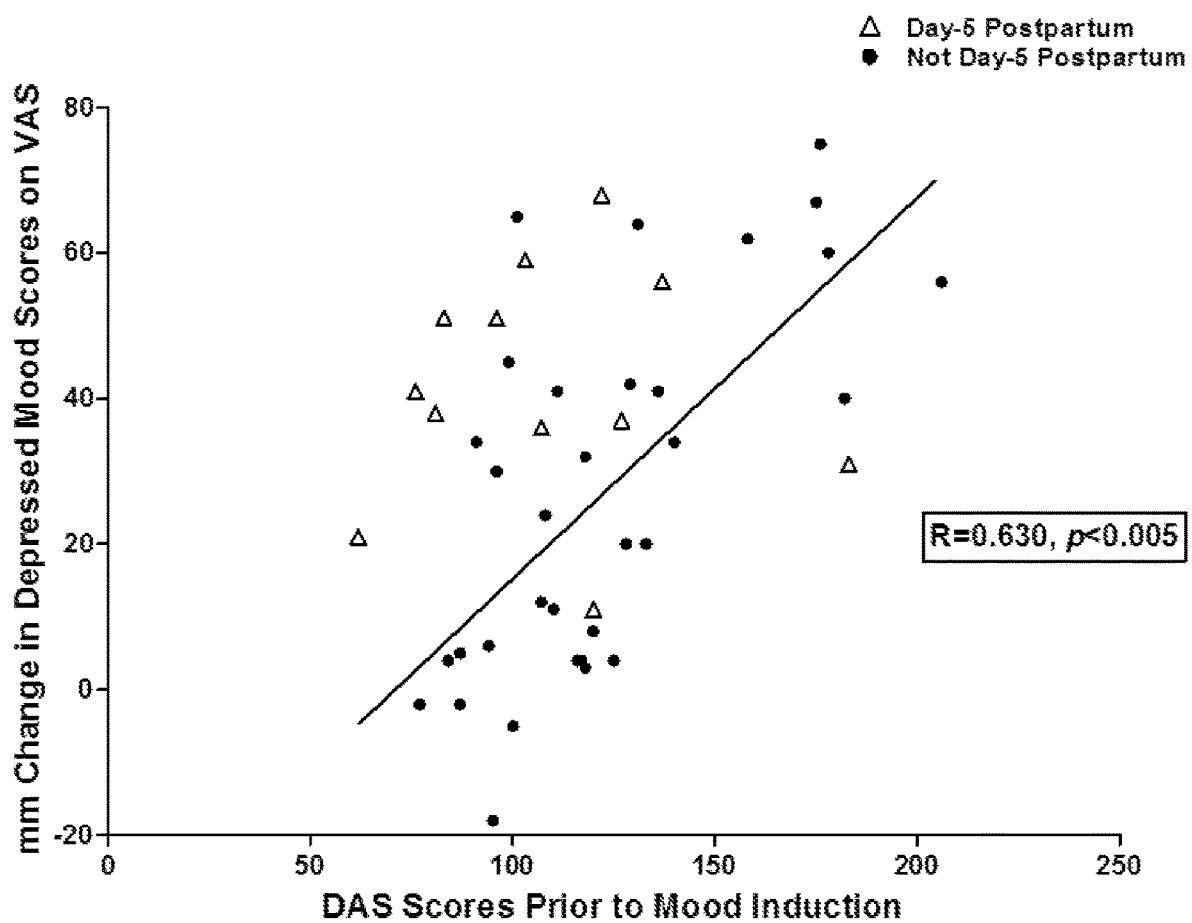
FIG. 1 is a chart showing correlation between depressed mood scores evaluated with Visual Analog Scale (VAS) scores and Dysfunctional Attitude Scale (DAS) scores prior to mood induction at day-5 postpartum.

There is provided herein a method of treating or preventing postpartum blues or depression comprising administering to a subject in need thereof: an antioxidant source; a tryptophan composition comprising from 1.0 g to 5.0 g of tryptophan; and a tyrosine composition comprising from 2.0 g to 50 g of tyrosine. Compositions and kits for use in the method are also described. Such a kit includes the antioxidant source, the tryptophan composition and/or the tyrosine composition together with instructions for use in the described method.

The antioxidant source used in the composition for treating or preventing postpartum blues or depression may comprise a food, a composition comprising a plant extract and an acceptable diluent, a vitamin, a micronutrient, and/or an anthocyanin. For example, the antioxidant source may comprise grapes, berries, citrus fruit, pomegranate, tomato, squash, carrot, sweet potato, a dark green vegetable, a beet, a leafy vegetable, a *Brassica oleracea* vegetable, a pepper, a melon, pineapple, lentils, a plant oil (optionally the plant oil may be one high in vitamin E), and/or a tree nut; and/or a juice, extract, or isolated antioxidant compound therefrom. For example, the antioxidant source may comprise blueberries, blueberry juice, blueberry extract, and/or an anthocyanin isolated from blueberry. The antioxidant source may comprise a precursor compound that is converted to an antioxidant form by the body after administration, for example the precursor compound may comprise cysteine. The antioxidant source may be one having an ORAC value at least about 3000 µmol TE/serving, for example at least about 5000 µmol TE/serving.

The tryptophan composition used in the composition for treating or preventing postpartum blues or depression may comprise L-tryptophan in free amino acid form or in a peptide form, and an acceptable diluent. The tyrosine composition used in the composition for treating or preventing postpartum blues or depression may comprise L-tyrosine in amino acid form and an acceptable diluent. Exemplary embodiments include 2 g of tryptophan in the tryptophan composition and/or 10 g of tyrosine in the tyrosine composition. With such exemplary embodiments, the antioxidant source may be one having an ORAC value of at least about 5000 µmol TE/serving, and comprising blueberries, blueberry juice and/or blueberry extract. The tryptophan composition, the tyrosine composition, and/or the antioxidant source may be in the form of a pill, a capsule, a tablet, a gel, a concentrate, a syrup, a bar, a cereal, a beverage, a shake, a powder, or a baked product.

A variety of options are available for the timing of administration to the subject in need of treating or preventing postpartum blues or depression, including but not limited to the following. The tryptophan composition may be administered on day-4 and the tyrosine composition on day-5 postpartum. The antioxidant source may be administered on more than one day from day-1 to day-5 postpartum. The antioxidant source may be administered on day-3, day-4, and day-5 postpartum. The antioxidant source may additionally be administered for 1-7 days following administration of the tryptophan composition. The antioxidant source may be administered twice daily. The antioxidant source may be administered to the subject for at least 2 to 5 treatment days. The tryptophan composition may be administered on the evening of the penultimate treatment day, simultaneously or following the administration of the antioxidant source; and the tyrosine composition may be administered on the final treatment day.

There is also provided herein a kit and a method addressing mood disorders such as depressed mood that may arise in the postpartum period, or in other periods associated with increased MAO-A levels, in a manner that improves mood or lessens the impact of the depressed mood on the individual. The method involves a multi-component administration regime in which the components, in combination, can reduce depressed mood. This can reduce the likelihood or severity of depressed mood during postpartum blues and/or depression for those at risk in the postpartum period, or can reduce sadness and depressed mood to enhance the lives of other subjects who may be experiencing depressed mood for other reasons. Further, depressed mood can be improved, deferred, or lessened in individuals susceptible thereto due to other conditions which increase MAO-A levels, such as in perimenopausal women, women within 18 months of delivering a baby, individuals experiencing or about to embark on smoking cessation, individuals experiencing depressed mood due to alcohol dependence and/or dependence withdrawal, and individuals with an alcohol use disorder such as alcohol abuse.

Addressing mood disorders may involve treatment and/or prevention. As used herein, "treatment" refers to addressing depressed mood in an individual already experiencing symptoms of and tendencies toward depressed mood in a manner that results in improvement. Improvement in sad mood may be referenced herein interchangeably with improvement in depressed mood. Treatment need not entirely cure or eradicate the depressed mood of the individual, but may simply lessen the strength or duration one or more of the symptoms such as dysfunctional attitude or crying. Improvement in mood may be determined by the individual, by a health care professional, or may be determined using accepted parameters such as surveys, questionnaires, or physiological tests for parameters such as MAO-A levels. Amelioration of symptoms without entirely eradicating depressed mood is considered as treatment. Treatment may be a reduction in severity or duration of symptoms as determined by self-reporting, or clinically accepted parameters used to assess depressed mood, including questionnaires or behavior evaluation techniques.

As used herein, "prevention" of depressed mood means addressing depressed mood prior to its occurrence in a manner that prevents, delays, or lessens the occurrence entirely or in part. Prevention also encompasses addressing depressed mood in advance of occurrence or in advance of severe onset in a manner that lessens the severity, duration, or likelihood of recurrence of the depressed mood and its symptoms, resulting in an improvement for the individual. "Prevention" does not mean that depressed mood will not occur in the individual, but indicates that measures are taken before depressed mood onset in an individual in order to address the problem in advance. There is benefit to the individual to having a preventative strategy in place prior to onset, which can be utilized proactively even if depressed mood can only be prevented in part. The term "prophylaxis" is used herein as having the same above-noted meaning as the term "prevention".

As used herein, the term "administration" of the antioxidant source, tryptophan composition or tyrosine composition may be self-administration by the subject, which may optionally be under the direction of another party such as a healthcare provider. Further, a product insert, label, or other available written source, such as provided as an on-line resource, may provide the direction for administration. Physical assistance with administration to the subject, such as by another party, including a personal assistant or health care provider is also encompassed.

As used herein the term "serving" is intended to mean the discrete form taken for ingestions of the antioxidant source, the tryptophan composition, or the tyrosine composition. A serving is typically referred to as the unit in which the source or composition is administered. The term "serving" is not intended to restrict or limit the form in which a composition or source is ingested, but rather is used to refer to as a single or discrete dose or portion. Thus, a serving may be a set amount of a food, food-like, or fluid substance, or may have the form of a powder, extract, pill or tablet.

As used herein, the term "day" generally means a calendar day. The phrase "the next day" is typically used to refer to the following calendar day, after a period that is utilized to obtain primary restorative sleep. However, for individuals who have recently given birth it should be understood that the period of time utilized to obtain primary restorative sleep may, at times, occur within a different portion of a calendar day than at night. In situations where such variability may occur, or for other reasons that involve shifted day-time and night-time schedules, the phrase "the next day" can be understood to mean the period of time following the individual's primary period of restorative sleep. Similarly, where "morning" or "evening" is referred to, the terms are meant to imply a time of day typically following or prior to, respectively, the individual's main restorative sleep period.

The term "antioxidant" as used herein refers to the capacity of a food or other substance included in the antioxidant composition, or may encompass a precursor compound which, upon consumption, is converted to an antioxidant within the body. One parameter for evaluating the capacity or strength of an antioxidant is the oxygen radical absorbance capacity (ORAC) value, as commonly reported within the food industry, as described in more detail below.

A method is described for treatment or prophylaxis of depressed mood in a subject with elevated MAO-A levels. The method comprises administering to a subject in need thereof: an antioxidant source once daily on at least day-1 of a treatment regime of from 3 to 5 days; wherein the antioxidant source comprises an anthocyanin-containing fruit, vegetable, nut, legume, or a juice or extract thereof, and has an ORAC value of at least about 3000 µmol TE/serving; a tryptophan composition on the evening of the penultimate day of the treatment regime, simultaneously or following the antioxidant source, said tryptophan composition comprising from 1.0 g to 5.0 g of L-tryptophan per serving in free amino acid form, and acceptable diluents; and a tyrosine composition on the final day of the treatment regime, administered the day after administering the tryptophan composition, said tyrosine composition comprising from 2.0 g to 50 g of L-tyrosine per serving in free amino acid form, and acceptable diluents.

The antioxidant source may comprise blueberries, blueberry juice, blueberry extract or a combination thereof, such as a blueberry extract together with blueberry juice.

Exemplary sources include grapes; berries; citrus fruit; pomegranate; tomato; squash; carrot; sweet potato; a dark green vegetable; a beet; a leafy vegetable; a *Brassica oleracea* vegetable such as cabbage, broccoli, cauliflower, kale, Brussels sprouts, savoy, or Chinese kale; a pepper; a melon; pineapple; lentils; a plant oil; a tree nut; and/or a juice, extract, or isolated antioxidant compound therefrom. The antioxidant source may optionally have an ORAC value of at least about 5000 µmol TE/serving.

The treatment regime may, for example, be one that is 3 days in duration, wherein the tryptophan composition is administered on the evening of day-2, and the tyrosine composition is administered on the morning of day-3. Optionally, the antioxidant source can be administered on two or more treatment days, such as each day of the treatment regime.

The method may additionally involve administration of the antioxidant source for periods before or after the treatment regime. For example the antioxidant source may be administered additionally for a period of from 1 to 10 days preceding or following the treatment regime, such as for 1, 2, 3, 4, 5, 6, 7, 8, 9 days, 10 days or more before or after the treatment regime.

In certain embodiments, the tryptophan composition may comprises about 2.0 g of L-tryptophan per serving, the tyrosine composition may comprise from 5.0 g to 20.0 g of L-tyrosine per serving, for example about 10 g of L-tyrosine per serving.

In an exemplary method, the tryptophan composition may consist of about 2 g of L-tryptophan per serving in free amino acid form, together with acceptable diluents; and the tyrosine composition may consist of about 10 g of L-tyrosine per serving in free amino acid form, together with acceptable diluents.

The tryptophan composition, the tyrosine composition, and/or the antioxidant source may be in the form of a pill, capsule, tablet, a gel, a concentrate, a syrup, a bar, a cereal, a beverage, a shake, a powder, or a baked product.

The subject with elevated MAO-A levels may be a postpartum subject, a subject experiencing excessive crying, a perimenopausal subject, or a subject with an alcohol use disorder or withdrawal therefrom. For example, the subject may be one experiencing excessive crying within 18-months postpartum, or one experiencing excessive crying beyond the 18-month postpartum period.

A method is described for treatment or prophylaxis of depressed mood in a subject experiencing excessive crying at up to 18-months postpartum, comprising administering to a subject in need thereof: an antioxidant source once daily on at least day-1 of a treatment regime of from 3 to 5 days; wherein the antioxidant source comprises an anthocyanin-containing fruit, vegetable, nut, legume, or a juice or extract thereof, and has an ORAC value of at least about 3000 µmol TE/serving; a tryptophan composition on the evening of the penultimate day of the treatment regime, simultaneously or following the antioxidant source, said tryptophan composition comprising from 1.0 g to 5.0 g of L-tryptophan per serving in free amino acid form, and acceptable diluents; and a tyrosine composition on the final day of the treatment regime, said tyrosine composition comprising from 2.0 g to 50 g of L-tyrosine per serving in free amino acid form, and acceptable diluents.

A kit is described herein for use in treatment or prophylaxis of depressed mood in a subject in need thereof. The kit includes at least one serving of an antioxidant source for administration on at least day-1 of a treatment regime of from 3 to 5 days; wherein the antioxidant source comprises an anthocyanin-containing fruit, vegetable, nut, legume, or a juice or extract thereof, and has an ORAC value of at least about 3000 µmol TE/serving; a serving of a tryptophan composition for evening administration simultaneously or following the antioxidant source on the penultimate day of the treatment regime; a serving of a tyrosine composition for administration on the final day of the treatment regime; and directions for use according to methods described herein.

The kit may include a serving of the antioxidant source in a multi-component form, comprising two or more of a fluid beverage, an extract, a crystal form and a powder form. The antioxidant source may, for example, comprise one or a combination of two or more of: grapes; berries; citrus fruit;

pomegranate; tomato; squash; carrot; sweet potato; a dark green vegetable; a beet; a leafy vegetable; a *Brassica oleracea* vegetable such as cabbage, broccoli, cauliflower, kale, Brussels sprouts, savoy, or Chinese kale; a pepper; a melon; pineapple; lentils; a plant oil; a tree nut; and/or a juice, extract, or isolated antioxidant compound therefrom.

A method of treating or preventing (prophylaxing) postpartum blues or depression is described in which the following are administered to a subject in need thereof. An antioxidant source is administered at least once between day-1 to day-5 postpartum; a tryptophan composition is administered on the evening of day-3 to day-5 postpartum, either simultaneously or following the first use of the antioxidant source; and a tyrosine composition is administered the day after administering the tryptophan composition.

The tryptophan composition may be administered on day-3 or day-4, which case and the tyrosine composition could then be administered on day-3, day-4 or day-5 postpartum, so as to be simultaneously (within the same day) delivered, or delivered the following day. The antioxidant source may be administered on more than one day from day-1 to day-5 postpartum.

The antioxidant source is administered on any one or more of day-1, day-2, day-3, day-4, and day-5 postpartum, and may be administered multiple times per day, for example: twice daily. While a serving is intended to be the unit dose of an administration, it is possible for the serving to be divided up over a day in instances where an individual may wish to do so by preference or by necessity.

Notably, the use of the antioxidant source by the subject can begin before the treatment regime begins, and can extend after the treatment regime. Thus, with pregnant subjects who may be due to give birth soon, the consumption of the antioxidant source may begin during pregnancy, rather than during the postpartum period, and may be consumed on a daily or periodic basis prior to the treatment regime period. The period of treatment with the antioxidant source may be extended beyond administration of the tyrosine and/or tryptophan compositions, for example by a period of from 1 to 7 days, or longer. Thus method described herein can begin prior to and extend beyond the treatment regime period of 3 to 5-days. Thus, the consumption of the antioxidant source for longer periods than the 3 to 5 day regime are possible, and within the scope of the method described.

Antioxidant Source Components and Quantity.

The antioxidant source may comprise a food, or may be a food component, or a non-food plant extract. The antioxidant source may comprise a composition with multiple ingredients, for example comprising a plant extract and an acceptable diluent. The diluent may be any food or pharmaceutical grade ingredient as would be known to a skilled person, and may assist in rendering the antioxidant source more palatable or desirable through enhancement of organoleptic properties.

Non-limiting examples of antioxidant sources include grapes, berries, citrus fruit, pomegranate, tomato, squash, carrot, sweet potato, dark green vegetables, beets, leafy vegetables, vegetables of the *Brassica oleracea* family (such as cabbage, broccoli, cauliflower, kale, Brussels sprouts, savoy, or Chinese kale), peppers, melons, pineapples, lentils, and tree nuts. Oils, such as plant oils, high in antioxidant may be used. For example, oils such as olive oil are high in vitamin E, known as an antioxidant source. Other vitamins or micronutrients having antioxidant capacity may be utilized as components of the antioxidant source. The antioxidant source may be a juice, extract, or isolated antioxidant compound isolated or extracted from one or more of these sources.

An example of an antioxidant source may be blueberries, blueberry juice, blueberry extract, and/or an anthocyanin isolated from blueberry, or any combination of these. Anthocyanin from other (non-blueberry) sources such as from other fruits, vegetables, legumes or nuts, may comprise the antioxidant source.

Foods known to be high in antioxidant capacity can be found based on standard accepted ORAC values of selected foods are available, discussed in more detail in the Examples. For example, select foods are listed in a USDA document prepared by Haytowitz et al., (2010). Foods listed in this document, shown to be high in antioxidants on a weight basis include: grapes, berries, citrus fruit, pomegranate, tomato, squash, carrot, sweet potato, dark green vegetables, beets, leafy vegetables, vegetables of the *Brassica oleracea* family, peppers, melons, pineapple, lentils and tree nuts such as almonds, hazelnuts, pecans, pistachios, and walnuts.

The ORAC content of the antioxidant source may be high in concentration (on a per weight basis), so that the antioxidant source is not excessive in volume. This will encourage subject compliance. A more concentrated antioxidant source may also have the advantage that fewer calories need to be consumed to ingest the desired amount of antioxidant per serving. Typically, the antioxidant source will have an ORAC value (Total ORAC μmol TE/serving) of at least about 3000 μmol TE/serving, for example, at least about 5000. The antioxidant source is typically derived from a food or extract that is high in antioxidants.

The antioxidant source may be in the form of an intact or extracted food, a pill, capsule, tablet, a gel, a concentrate, a syrup, a bar, a cereal, a beverage, a shake, a powder, or a baked product.

Further, the antioxidant source may comprise antioxidant precursors, which are compounds that are metabolized by the body become an antioxidant compound. For example, cysteine may be considered an antioxidant precursor.

A typical serving size for the antioxidant source may comprise blueberry-derived components, such as an extract in powder or liquid form, or a juice. For example, the antioxidant source may be a blueberry-based beverage comprising blueberry juice (or a juice concentrate) to which a blueberry extract may be added in powdered form. When used, the extract may be one that is highly concentrated, to which much of the antioxidant effect may be attributed. Typically, a beverage volume would range from 200 to 400 mL, and the taste and mouthfeel would be one that appeals to subjects in a manner that is similar to drinking a fruit juice or a fruit smoothie. Palatability may assist with compliance of individuals, and thus a beverage that is not too concentrated or dilute may appeal to subjects during the postpartum period.

The serving size for any portion of the antioxidant source may be determined on a standard basis for all individuals, or may be adjusted to suit one or more individualized parameter, such as based on a determination of an individual's daily caloric (energy) requirements, activity levels, or based upon body weight parameters as desired such as lean body mass, BMI, or body weight pre-pregnancy, during pregnancy or post pregnancy.

Serving size may be expressed on a serving size basis, or may be adjusted to be expressed on a dose per body weight basis such that a dose is calculated based on body weight, such as pre-pregnancy, during pregnancy, or on the day of delivery of the serving. Further, dose may be estimated and adjusted based on a calculated or assumed daily caloric intake basis, in which case individuals with a higher caloric intake who may be more active, may consume a larger daily amount than individuals who are more sedentary.

Servings of the antioxidant source may also be adjusted to include optional ingredients to render the treatment more palatable to the subject, such as flavorings, coloring, sugar or other sweeteners (if sugar is not desired), or thickener. Servings may be consumed with other ingredients, such as with an unrelated food product or together a meal. Further, servings may be integrated with such other food products.

The Tryptophan Composition.

The tryptophan composition comprises L-tryptophan, and may be in amino acid form (which may be in a free form or in a salt form) or in a peptide form. The tryptophan is present in the composition together with and an acceptable diluent as may be used in a food product or in a drug formulation, depending on the form the composition takes.

According to certain methods described herein, the tryptophan composition may be utilized with the antioxidant source for administration to a subject without use of the tyrosine composition. According to certain other methods described herein, the use of the tryptophan composition is only optional.

When used, tryptophan composition comprises from 0.5 g to 50.0 g of L-tryptophan per serving, for example from 0.5 to 20 g per serving, from 1 to 20 g per serving, from 1 to 00 g per serving, or from 1 to 5 g per serving. An exemplary embodiment may have 2 g tryptophan per serving.

If the quantity per serving is to be individualized, and expressed for example on a per body weight basis. Based on the assumption of a typical pre-pregnancy body weight ranges from 45-110 kg, the range of acceptable serving sizes may be expressed accordingly. A typical calculation based on a unit serving size of from 0.5 g to 50 g of L-tryptophan per serving may be adjusted to be expressed as a broader range, such as from 4.5 mg/kg (when a low quantity is selected and a subject has a high body weight) to 1.11 g/kg (when a high quantity is desired and a subject has a low body weight). These ranges encompass optimal exemplary quantity of from 1 to 20 g per serving. Mixed or isolated protein, or a protein hydrolysate may be used to achieve the tryptophan content.

The composition may be in the form of a pill, capsule, tablet, a gel, a concentrate, a syrup, a bar, a cereal, a beverage, a shake, a powder, or a baked product.

High tryptophan intact protein sources, such as from turkey meat, may be used as components of the tryptophan composition.

The serving size for the tryptophan composition may be determined on a standard basis for all individuals, or may be adjusted to suit one or more individualized parameter, such as based on a determination of an individual's caloric (energy) requirements, activity levels, or based upon body weight parameters as desired such as lean body mass, BMI, or body weight pre-pregnancy, during pregnancy or post pregnancy.

The tryptophan composition may also be adjusted to include optional ingredients to render the treatment more palatable to the subject, such as flavorings, coloring, sugar or other sweeteners (if sugar is not desired), or thickener. The tryptophan composition may be consumed with other ingredients, such as with an unrelated food product or together a meal. Further, servings may be integrated with such other food products.

The Tyrosine Composition.

The tyrosine composition comprises L-tyrosine, and may be in amino acid form (which may be in free form or a salt form) or in a peptide form. The tyrosine is present in the composition together with and an acceptable diluent as may be used in a food product or in a drug formulation, depending on the form the composition takes.

According to certain methods described herein, the tyrosine composition may be utilized with the antioxidant source for administration to a subject without use of the tryptophan composition. According to certain other methods described herein, the use of the tyrosine composition is only optional.

When used, exemplary levels in the tyrosine composition are from 1.0 g to 100 g of L-tyrosine per serving, such as from 1.0 g to 50.0 g, from 2.0 g to 50.0 g, or from 5 g to 20.0 g of L-tyrosine per serving. An exemplary amount may be about 10 g per serving.

If the quantity per serving is to be individualized, and expressed for example on a per body weight basis. Based on the assumption of a typical pre-pregnancy body weight ranges from 45-110 kg, the range of acceptable serving sizes may be expressed accordingly. A typical calculation based on a unit serving size of from 1.0 g to 100 g of L-tyrosine per serving may be adjusted to be expressed as a broader range, such as from 9 mg/kg (when a low quantity is selected and a subject has a high body weight) to 2.2 g/kg (when a high quantity is desired and a subject has a low body weight). These ranges encompass optimal exemplary quantity of from 5 to 20 g per serving.

The composition may be in the form of a pill, capsule, tablet, a gel, a concentrate, a syrup, a bar, a cereal, a beverage, a shake, a powder, or a baked product.

Substances such as phenylalanine can be converted to tyrosine by the body, and thus it is understood that phenylalanine may be a substitute in desirable instances. It may not be desirable to utilize phenylalanine (or 5-hydroxytryptophan) in women who are nursing if it is undesirable to increase breast milk content of the substance.

High tyrosine intact protein sources may be used as components of the tyrosine composition. Thus, a mixed or isolated protein, or a protein hydrolysate may be used as a source of tyrosine.

The serving size for the tyrosine composition may be determined on a standard basis for all individuals, or may be adjusted to suit one or more individualized parameter, such as based on a determination of an individual's caloric (energy) requirements, activity levels, or based upon body weight parameters as desired such as lean body mass, BMI, or body weight pre-pregnancy, during pregnancy or post pregnancy.

The tyrosine composition may also be adjusted to include optional ingredients to render the treatment more palatable to the subject, such as flavorings, coloring, sugar or other sweeteners (if sugar is not desired), or a thickener. The tyrosine composition may be consumed with other ingredients, such as with an unrelated food product or together with a meal. Further, servings may be integrated with such other food products.

Kits Containing Multiple Components.

The antioxidant source, the tyrosine composition, and the tryptophan composition (when present), may be combined as a multi-component kit for use in treating or preventing/prophylaxis of postpartum blues or depression. When used specifically for the day-5 postpartum window, such a kit comprises at least one serving of the antioxidant source for administration between day-1 to day-5 postpartum; the tryptophan composition for evening administration simultaneously or following the antioxidant source between day-3 to day-5 postpartum; and the tyrosine composition for administration the day after administering the tryptophan composition.

When such a kit is intended for use during periods within and outside of the day-5 postpartum period, for example up to and including 18-months postpartum for women experiencing crying episodes that do not meet the criteria for a full major depressive episode, then the content of the kit and instructions may be adapted accordingly. The tryptophan (when present) and tyrosine compositions may be provided individually, for example in packaging such as a foil blister pack, a small vial, or another acceptable form of encasement. The antioxidant source, such as an extract (or more specifically blueberry extract), may be provided in a powdered form within the kit. As such, the powder may be encased in an envelope that is easily opened by the user, or as a compressed tablet that can be readily dissolved in a beverage or be chewed by the consumer. The extract may also be provided in a concentrate form, that can flow as a thick liquid or gel, and thus would be encased in a manner appropriate for such liquids or gels, such as in a squeezable tube, or a plastic or foil encased envelope.

Such kits may include a fluid beverage, such as for example blueberry juice. Alternatively, the kit may simply direct the user to juices that are available for purchase separately, which may permit the kit to be lighter in weight, having a shelf life and expiry date that is longer than the shelf life of a juice, and may be made more amenable to shipping. One advantage of including a specific juice in the kit is that all necessary ingredients for a TTB regime (such as described herein below in the Examples) are ready at the user's convenience. One advantage of not including a specific juice in the kit is that the user may select her own brand of juice depending on preference and availability, and may be able to purchase the juice in bulk, so as to reduce packaging requirements necessitated by individual servings, thereby acknowledging the environmental issues surrounding packaging. Both such kits are envisioned: with and without a fluid beverage component included.

The kit instructions may be specifically directed toward women in the postpartum period, either at day-5 or past day-5 postpartum. However, should the kit be directed to users who are not experiencing postpartum blues or depression, but who wish to take the supplement regime for addressing depressed mood resulting from a condition that results in elevated MAO-A levels, then the regime may simply be stated with a day-based cycle, for example using a day-1 to day-5, or day 1 to day-3 cycle, wherein day 1 is determined as the day closest to a crying event (rather than parturition as the determinant of day-1). The instructions may state for the user a specific window of time based on hours of the day, in which to consume each component of the kit.

Alternatively, the user may be directed to calculate the time of day, based on their own individual sleeping patterns. This may permit individuals with varying waking-sleeping schedules to adapt the timing of consumption to a time that is optimal for them. For example, a person who has irregular sleeping patterns in the period of time following the birth of a child may wake for the day at 5 am, whereas another may wake for the day at 8 am, depending on the child's sleeping patterns. Outside of day-5 postpartum, people may have shift work or other factors of influence, which determine their waking time. The kit instructions may thus direct a user to take the supplements at certain hours following their morning waking time, rather than by the precise time of day determined on the clock.

Such a kit may contain directions for use according to the methods described herein. The kit may include multiple components for the antioxidant source, so that two or more components may be mixed or ingested simultaneously or separately by the subject. An example of this would be a juice and a crystal or powder extract that is to be added to the juice just prior to consumption, whether the juice is included in the kit, sold separately, or obtained at the discretion of the user.

By "instructions" or "directions" to be included in a kit, this encompasses a written paper insert, on-line instructions provided to a user after signing in to a website (in the case where no paper insert is needed), or may be provided as a service using telephone directions such as automated text messages prompting a user to consume the supplement, or a telephone call from a service center that may be staffed by workers. Any form of communication with a user may be encompassed as "instructions" or "directions", if it prompts, reminds, or instructs the user about how to utilize the kit.

Frequency of Use: Discrete Use and Repeated/Cycles.

For individuals experiencing, or susceptible to experiencing postpartum blues or depression, or for individuals showing elevated MAO-A levels unrelated to parturition, the use of the method described herein, such as the specific TTB supplementation regime described in the Examples, may be conducted as a discrete (or one-time-only) use, such as in the day-5 postpartum period, for one pregnancy, or for subsequent pregnancies. However, as shown in the Examples below there may be benefits to the method used within 18-months postpartum that can be realized on an ongoing basis when crying is experienced, and depressed mood is expected. Thus, an individual may follow the regime either on a discrete basis, or by using repeated cycles of the regime, to address ongoing or recurring periods of time. For individuals with elevated MAO-A levels who may experience crying or depressed mood on a periodic or recurring basis, use of the method described need not be limited to a one-time use, but can be repeated on an ongoing basis.

A kit could include instructions advising on optimal frequency of use, for individuals who experience ongoing crying or depressed mood.

Addressing Depressed Mood Associated with MAO-A Elevated Levels.

A method is provided for treating or preventing depressed mood in subjects with elevated MAO-A levels. Such subjects may include perimenopausal women, women within 18 months of delivering a baby but outside of the immediate 6 days of the postpartum period, individual experiencing depressed mood or expecting to experience it as a result of undertaking smoking cessation, or an individual alcohol dependence, among others. In these instances, the method can commence with the onset of symptoms or at the onset of undertaking an activity expected to bring on symptoms (such as when initially quitting smoking). The method involves administering to the subject the antioxidant source for 2 to 5 treatment days; an optional tryptophan composition is administered on the evening of the penultimate treatment day of a set treatment of determined length up to six days, which may begin on day-1 of treatment when the treatment is set to last only 2 days. Subsequently, a tyrosine composition is administered on the final treatment day. For example, in a 5-day treatment regime, the tryptophan composition can be administered on treatment day-4 and the tyrosine composition is then administered on treatment day-5. Optionally, the antioxidant source may be administered twice daily during the span of the treatment period.

It has been found by the inventor that monoamine oxidase-A (MAO-A) VT, an index of MAO-A density, is increased in the prefrontal and anterior cingulate cortex, during postpartum depression and when a depressed mood spectrum symptom appears, specifically: when greater predisposition to crying is present. MAO-A is an enzyme that increases in density after estrogen decline, and has several functions including creating oxidative stress, influencing apoptosis and monoamine metabolism. The inventor has found (not shown here) that in a cohort of women including 15 first onset, antidepressant naive, postpartum depression subjects, 12 postpartum healthy subjects who cry due to sad mood, 15 asymptomatic postpartum healthy women and 15 healthy women not recently pregnant were assessed (data not shown), the subjects having postpartum depression and greater predisposition to crying also had greater MAO-A VT levels in the prefrontal and anterior cingulate cortex. Greater MAO-A VT may thus be useful as a biomarker to determine individuals who may derive particular benefit from the method described herein, or more particularly the TTB regime described in the Examples.

The use of the antioxidant source, the tryptophan composition, and the tyrosine composition is provided for treating or preventing (referenced herein as being prophylactic of) postpartum blues or depression in a subject who is experiencing symptoms or who is susceptible to experiencing such symptoms. The source and compositions may also be used in the preparation of three separate medicaments for use as described herein. Such medicaments may be combined in a commercial package together with instructions for use.

Use of the antioxidant source, the tryptophan composition, and the tyrosine composition is provided for treating or preventing depressed mood in subjects with elevated MAO-A levels. The elevated MAO-A levels may be evaluated for elevation against a subject's own previous measurements taken at a different period in life when no symptoms of depressed mood were evident, or the MAO-A levels of an individual may be evaluated against accepted population standards based on appropriate comparable demographics.

Overview of Model Used in Evaluation of Mood.

FIG. 1 provides a chart reproduced from Dowlati et al. (2014), showing correlation between changes in depressed mood scores on a VAS scale versus DAS scores prior to mood induction. Triangles represent subjects at day-5 postpartum, while other scores obtained outside of day-5 postpartum are represented by circles. A significant correlation exists between the Dysfunctional Attitude Scale (DAS) scores prior to mood induction and the change in depressed mood scores evaluated on a Visual Analog Scale (VAS) (R=0.630, p<0.005), verifying the VAS scale as an indicator of depressed mood. Changes in VAS can be evaluated by reference to a self-reported marking of mood on a visual analogue scale comprising a 100 mm line. Change in VAS can be used to assess changes in mood before and after induction of depressed mood. No treatment (other than depressed mood induction) was given to subjects shown in FIG. 1. The greater the severity of dysfunctional attitudes, the greater the change in VAS toward depressed mood after mood induction.

Women at day-5 postpartum are particularly susceptible to mood changes upon depressed mood induction. Day-5 showed a stronger elevation in depressed mood scores in Visual Analog Scale (VAS) upon induction, as compared with postpartum subjects within 18 months of delivery, but outside of day-5 (Dowlati et al., 2014). This makes day-5 a particularly important day when considering whether a woman may experience postpartum blues or postpartum depression, and an optimal time to consider options for treatment and prevention/prophylaxis.

Application to Other Conditions Associated with Elevated MAO-A. Individuals experiencing depressed mood due to other conditions, including perimenopause, individuals prone to crying (such as within 18 months of delivering a baby), individuals experiencing smoking cessation or anticipating quitting smoking as a preventative measure, individuals in alcohol dependence withdrawal, or an individual with an alcohol use disorder, such as persons experiencing depressed mood due to alcohol abuse, can utilize the method described herein.

The treatment may begin when an individual begins to experience exceptional feelings of depressed mood based on dysfunctional attitude, crying or other emotional/cognitive indicators, or treatment may be instigated if elevated MAO-A levels are observed. The regime may be as described above, with day-1 being the day on which the antioxidant-containing food or source is provided. The above-described method can be utilized as multi-day treatment at the onset of depressed mood, and/or when MAO-A levels are elevated. Extending the use of the antioxidant source beyond the use of the tryptophan and/or tyrosine compositions for 1 to 7 subsequent days may further assist in improving or avoiding depressed mood.

Elevated MAO-A is observed in women during perimenopause who are experiencing depressed mood. High levels of MAO-A have also been observed in individuals experiencing the depressed mood of alcohol dependence and smoking cessation.

Women nearing menopause, or in perimenopause, have higher levels of monoamine oxidase-A than younger women and menopausal women. In a study of women aged 41-51, elevated levels of the chemical monoamine oxidase-A (MAO-A) were observed, which may contribute to high rates of first-time depression seen among women in this transitional stage of life (Rekkas et al., 2014, which is incorporated by reference herein). During perimenopause, a common symptom is mood change such as increased crying. Rates of first-time clinical depression among this group may be about 16%, and a similar number of individuals may experience milder depressive symptoms.

To investigate the relationship between MAO-A levels and the mood changes during perimenopause, brain imaging using positron emission tomography (PET) was conducted in three groups of women: those of reproductive age (n=19), in perimenopause (n=27), and in menopause (n=12). Levels of MAO-A were 34% higher in women with perimenopause than in the younger women, and 16% higher than those in menopause.

The women in perimenopause also reported a higher tendency to cry, based on an Adult Crying Inventory questionnaire. This tendency was associated with high MAO-A levels in the prefrontal cortex of the brain. MAO-A levels were reduced during menopause, once fluctuating levels of estrogen stabilized. The method described herein can be utilized in treatment, prevention (similarly referenced herein as "prophylaxisis") or amelioration of depressed mood for perimenopause subjects, as well as other subjects experiencing depressed mood corresponding with elevated MAO-A.

Example 1

Effect of Treatment on Day 5 Postpartum Subjects Versus Crying Spell Subjects at 18-Months Women at day-5 postpartum were enrolled in a study to observe the effect of a multi-day protocol according to the method described herein, on susceptibility to depressed mood induction, for comparison with women known to experience crying spells within 18 months of birthing who were also treated with the described protocol. The treatment protocol showed improvement in the day-5 susceptibility to depressed mood induction for postpartum subjects.

Participants, Study Design, and Methodology.

Women aged 18 to 45 were recruited through advertisement. Subjects were healthy, medication-free, and not taking any investigational products.

Subjects were grouped as day 5 postpartum, versus women within 18 months of giving birth that reported crying spells but did not have symptoms of a major depressive episode. Since a priori the levels of dysfunctional attitudes were unknown in the subjects sampled, it was anticipated that self-reported crying spells would be more likely to sample women with higher levels of dysfunctional attitudes. Subjects were thus grouped as criers, or not reporting crying spells. For the control group not receiving the supplementation protocol, 12 women (mean age 32.75±3.39) were enrolled as the day-5 postpartum group and 11 women (mean age 29.09±4.18) were enrolled who were within 18 months postpartum reporting vulnerability towards crying (the criers). Four subjects were in the day-5 test group consuming the compositions referenced herein as TTB, and two criers were in the TTB test group. "TTB" indicates the instant test protocol, and stands for: Tryptophan Tyrosine Blueberry.

Administration of the Visual Analog Scale (VAS), was conducted initially, and following a break, subjects underwent the sad mood induction protocol (MIP) and VAS was repeated. Further protocol details were as reported by Dowlati et al. (2014). The VAS involves a 10-point scale visual analog scale with 8 items consistent with how subjects feel in the moment. The 8 items included depressed, happy, restless, sad, anxious, angry, drowsy and alert.

The Mood Induction Protocol (MIP) typically involves two forms of mood induction: neutral and sad (or depressed) mood induction. To induce sad and neutral mood states the Velten (1968) MIP was used in combination with the approach of Clark (1985). The Velten method is the most widely used technique for studying affective influences upon behavior and it has demonstrated effectiveness in altering subjective emotional states. Velten MIP is a series of 60 self-referent statements. Negative statements reflected pessimism, dissatisfaction, and lethargy; for example "life is a heavy burden". Neutral statements example are such as "an orange is a citrus fruit". Subjects were asked to read each statement, printed individually, first to themselves and then aloud, and to 'feel and experience each statement as it would apply to you personally'. In addition, to facilitate the mood induction, participants were also presented with a piece of music while reading the statements (Clark, 1985). For sad/depressed mood induction, subjects listen to Prokofiev's "Russia under the Mongolian Yoke" and for neutral mood induction, subjects listen to Mozart's "Piano Concerto No. 21 in C Major".

The following regime was utilized in subjects receiving TTB treatment (TTB is used herein to represent the instant protocol involving Tryptophan Tyrosine and Blueberry). The antioxidant source was administered to subjects on day-3, day-4 (twice), and day-5 postpartum. The tryptophan composition comprising L-tryptophan (2.0 g) was administered at night on day-4 postpartum (tryptophan obtained from Apotex, Canada). The tyrosine composition comprising L-tyrosine (10.0 g) was administered on the morning of day-5 postpartum (tyrosine obtained from Trophic Canada).

Table 1 outlines the composition of the antioxidant source, which is based on blueberry juice and blueberry extract. The composition was administered on postpartum day-3 night-time, day-4 daytime (morning), day-4 night-time, and day-5 daytime (morning), to each subject. Two components of the composition are detailed below, first a beverage component "A", and secondly a sachet component "B" containing powder.

The sachet component contains a blueberry extract powder (VitaBlue™) and was obtained from FutureCeuticals™ of Momence, Ill. The amount used in the composition contains the equivalent to about a cup of blueberries. Additional details of dosing and subject protocol are found below in Example 2.

TABLE 1

Composition of Antioxidant Source

| | Ingredient | Supplier (Code) | % by weight | Weight in Batch (g) |
|---|---|---|---|---|
| | | | | 355 |
| A - Beverage Component | water | GFTC | 79.62 | 282.64 |
| | Blueberry Juice Concentrate | Milne Fruit (Prof. Ing) | 10.00 | 35.50 |
| | Blueberry Flavour | Bell (18039) | 0.75 | 2.66 |
| | Bordeaux Colour | GNT | 0.00 | 0.00 |
| | Sugar | Red Path | 6.00 | 21.30 |
| | Citric Acid | Cambrian Chemicals | 0.10 | 0.36 |
| B - Sachet Component | Sugar | Red Path | 3.25 | 11.54 |
| | VitaBlue ™ | FutureCeuticals (N208) | 0.28 | 1.00 |
| | | Totals: | 100.00 | 355.00 |

A 2% overage was applied to the ingredients as provided to individuals in the study, to compensate for residual losses inherent in food consumption.

At each use in the designated time course, the subjects were given 355 g of the composition to consume.

Antioxidant capacity was quantified in the antioxidant source using standard food industry Oxygen Radical Absorbance Capacity (ORAC) testing. The ORAC test is routinely used to quantify antioxidant content of foods and other products. The antioxidant source components outlined in Table 1 were evaluated in the standard ORAC test to determine oxygen radical absorbance capacity (or antioxidant capacity) for component "A" alone, and for components "A" and "B" in combination. Standard accepted ORAC values of selected foods are available, for example, from Haytowitz et al., (2010).

The ORAC assay measures the degree of inhibition of peroxy-radical-induced oxidation by compounds present in a fluid milieu. It measures a value as Trolox equivalents (TE), which encompasses inhibition time and the extent of inhibition of oxidation. The method is described in more detail by Prior et al. 2003, which is herein incorporated by reference.

Table 2 shows the results of the ORAC test, to approximate antioxidant capacity of the source. Beverage component A was tested in a single sample, while for the combined "A" and "B" components were tested. A high level of antioxidant capacity was confirmed in the antioxidant source ("A"+"B")

subjects were advised to drink a serving of the blueberry juice ("A") with blue berry extract ("B"), which together serve as the antioxidant source. On the morning of day-4 postpartum, subjects again consumed another serving of the antioxidant source ("A" and "B"). On the night of day-4 postpartum the subjects consumed another serving of the antioxidant source ("A" and "B"), and were additionally instructed to self-administer the tryptophan composition containing 2 g L-tryptophan. For the components consumed on day-3 and day-4, subjects self-administered the appropriate compositions at home. To ensure compliance, subjects were provided a reminder phone call at the appropriate time for each of the components to be consumed. For day-5 consumption, subjects came to a clinic at the Centre for Addition and Mental Health (Toronto, Canada) to consume the designated components outlined in the Day-5 entry shown in Table 3. Subjects arrived at approximately 8:30 am to receive the tyrosine composition containing 10 g L-tyrosine), concurrent with consumption of another serving of the antioxidant source ("A" and "B").

TABLE 3

Timing of Administration of Kit Components

| Postpartum Day (time of day) | Approximate Time (location) | Activity |
| --- | --- | --- |
| Day-3 postpartum (night) | 9:00 pm (at home) | Antioxidant Source ("A" and "B" containing blueberry extract + blueberry juice) |
| Day-4 postpartum (morning) | 10 am (at home) | Antioxidant Source ("A" and "B" containing blueberry extract + blueberry juice) |
| Day-4 postpartum (night) | 9:00 pm (at home) | Tryptophan composition (2 g L-tryptophan); and Antioxidant Source ("A" and "B" containing blueberry extract + blueberry juice) |
| Day-5 postpartum (morning) | 8:30 am (at CAMH) | Tyrosine composition (10 g L-tyrosine); and Antioxidant Source ("A" and "B" containing blueberry extract + blueberry juice) |

TABLE 2

ORAC Values of Antioxidant Source and Component

| Sample | Study Element | Value |
| --- | --- | --- |
| Beverage Component "A" | ORAC μmol TE/100 g | 595 TE/100 g |
| Combined Components "A" and "B" | ORAC μmol TE/100 g | 1875 TE/100 g |

In this instance, the antioxidant capacity of the antioxidant source was 18.75 TE/g, and thus the estimated antioxidant capacity for each 355 g serving can be calculated as about 6,656.

Table 3 outlines the timing with which subjects self-administered the antioxidant source, the tryptophan composition, and the tyrosine composition. Subjects were provided with a kit containing blueberry juice (beverage component "A") the blueberry extract (a sachet containing VitaBlue™ extract, component "B") and the tryptophan composition containing L-tryptophan. On the night of day-3 postpartum, Following consumption of the day-5 treatments, the reporting of depressed mood by VAS (baseline) was obtained, followed by depressed mood induction as described above, and a subsequent reporting of VAS was obtained. The depressed mood induction procedure, as described above, was in accordance with the protocol described by Dowlati et al., (2014).

Figure 2:
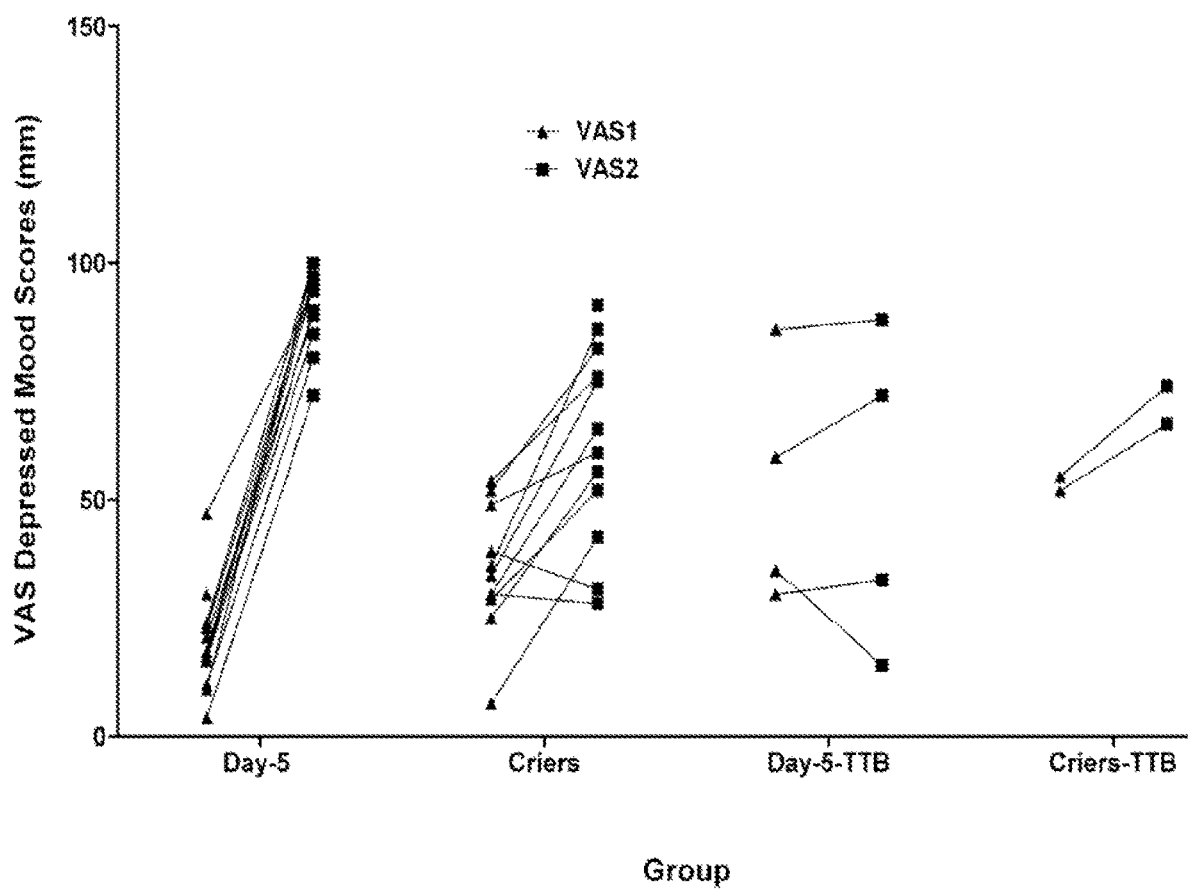
FIG. 2 is a chart showing Visual Analog Scale (VAS) depressed mood scores of individuals before and after a mood induction treatment at day-5 postpartum with and without treatment, and makes comparison with individuals known to cry easily within 18-months postpartum.

FIG. 2 illustrates the data obtained. The chart shows Visual Analog Scale (VAS) depressed mood scores of individuals before and after mood induction treatment at day-5 postpartum with and without treatment, and makes comparison with individuals known to cry easily within 18-months postpartum.

The first set of data (labeled "Day-5") shows the change in VAS following mood induction, illustrating a consistent susceptibility to a negative change in mood at day-5 postpartum, indicative of heightened susceptibility to a depressive episode. The subjects in this data set did not undergo the treatment regime.

The second set of data (labeled "Criers") shows the change in VAS following mood induction for subjects who are known to cry readily but are not clinically depressed. The mood induction took place within 18 months of delivery for this group, but not on day-5 postpartum. The subjects in this data set did not undergo the treatment regime. Criers outside of Day-5 also showed susceptibility to a negative change in mood following mood induction, indicative of susceptibility to a depressive episode.

The third set of data (labeled Day-5-TTB) shows no consistent change in VAS scores following mood induction on Day-5 for individuals having the treatment according to the method described above ("TTB" indicating Tyrosine Tryptophan Blueberry). Importantly, the trend toward induced negative mood at day 5 which was highly pronounced in the day-5 subjects in the first data set (no treatment) is not seen in the day-5 subjects who underwent treatment according to the described method. This is a significant improvement, given that increased depressive mood scores for this group may be a good indicator of onset of postpartum blues or postpartum depression.

The fourth set of data (labeled Criers-TTB) shows no consistent change in VAS scores following mood induction for criers (individuals susceptible to excessive crying with 18 months of delivery), following the treatment according to the method described above ("TTB"). Importantly, the trend toward induced negative mood observed in criers without treatment (second set of data) is not seen in the criers who participated in treatment according to the described method. This is a significant improvement, given that increased depressive mood scores upon induction may be a predictor of onset of a depressive episode for this group.

These data indicate that participating in the regimen outlined herein, of consuming the antioxidant source, (in this case, 4 servings at about 6000 ORAC µmol TE/serving, together with the tryptophan composition containing L-tryptophan and subsequently the tyrosine composition containing L-tyrosine, can improve outcomes upon mood induction in a manner that would reduce susceptibility to postpartum blues and postpartum depression. Specifically, a depressed mood was not induced at day-5 postpartum in the individuals receiving the treatment, whereas a depressed mood was consistently induced in those day-5 individuals who did not receive the described treatment.

Figure 3:
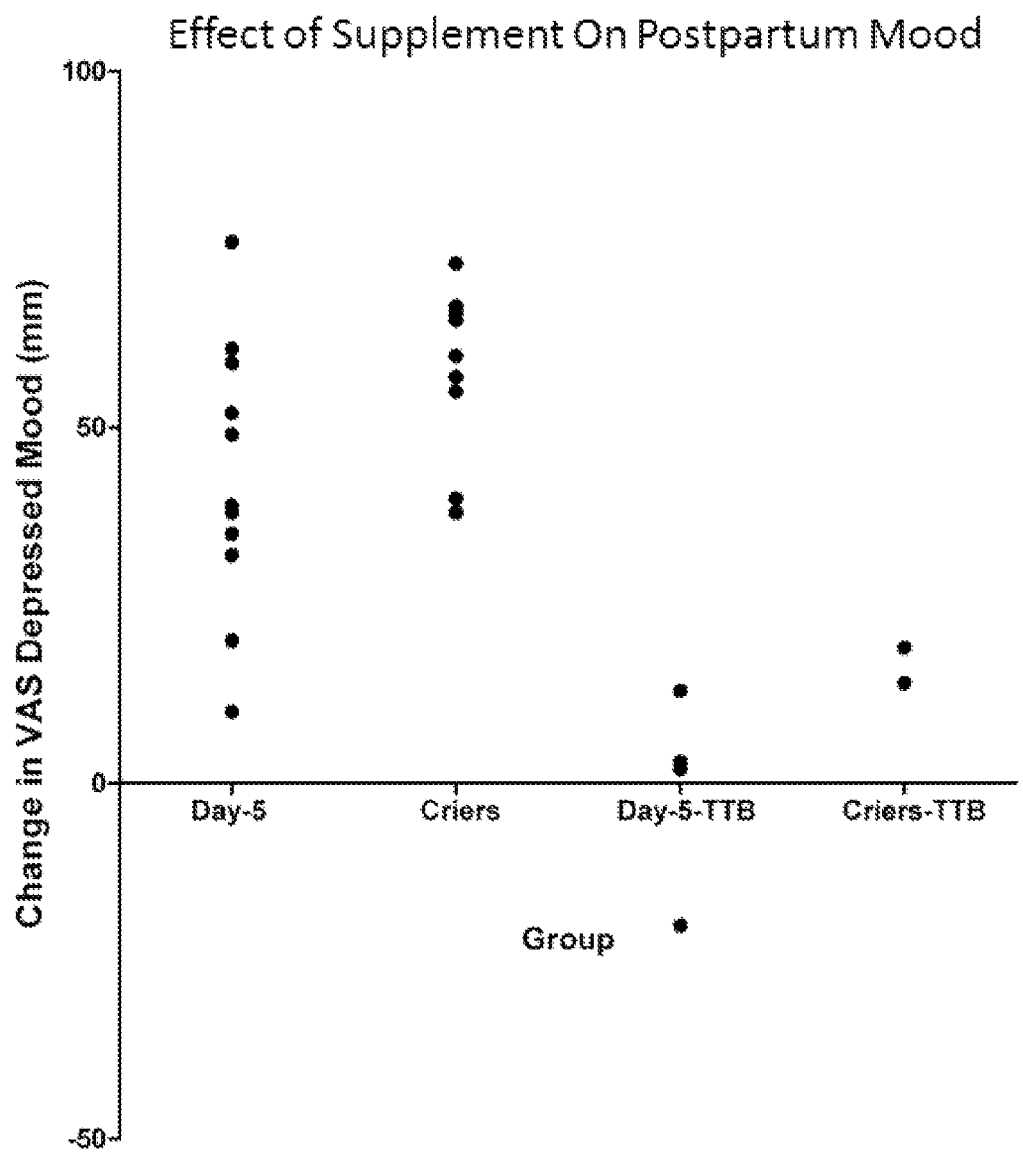
FIG. 3 is a chart showing the change in score from the baseline Visual Analog Scale (VAS) scores following mood induction treatment at day-5 postpartum with and without treatment, and makes comparison with individuals known to cry easily within 18-months postpartum.

FIG. 3 is a chart showing the data for these four subject groups, expressed as change from baseline score in the Visual Analog Scale (VAS) depressed mood scores of individuals following mood induction treatment at day-5 postpartum with and without treatment, and makes comparison with individuals known to cry easily within 18-months postpartum. These data further emphasize that treatment ("TTB" groups) was of benefit at Day-5 postpartum, as well as to criers tested outside of day-5. Even after the mood induction treatment, those subjects receiving the treatment exhibited a markedly more stable mood upon exposure to mood induction, with minimal movement of the self-reported score in depressed mood along the 100 mm line.

Stability in mood, even in the face of an inducing event is particularly desirous at day-5 postpartum when susceptibility to postpartum blues and postpartum depression is most heightened. However, stability in mood also has benefits outside of day-5, in that an individual experiencing a depressed mood may be less susceptible to induction of a depressive episode when exposed to external factors in her ambient environment.

The stability associated with the treatment regime described herein has benefit to individuals susceptible to or experiencing depressed mood, or individuals for whom MAO-A levels are elevated.

Example 2

Supplemented Subjects Show Greater Resilience to Depressed Mood Induction at Day 5 Postpartum In this Example, it is shown that women treated with the supplement protocol described herein show greater resilience to depressed mood induction day-5 postpartum.

Postpartum depression (PPD) is a common complication of childbearing. Major depressive disorder is a common cause of death and disability in women. Postpartum depression has impact upon child care, return to work, and elevates the risk of future major depressive episodes (MDE). Risk for PPD is influenced by clinical history, as well as psychological, social and biological factors.

This Example provides a protocol of dietary supplementation with the amino acids tyrosine and tryptophan along with blueberry extract (an antioxidant) for reducing the intensity of postpartum blues and sadness during postpartum. Severity of postpartum blues is predictive of risk for postpartum depression, so reducing severity of postpartum blues may prevent/prophylax postpartum depression (PPD), based upon a biological model of excessive monoamine metabolism. With the loss of placenta, there is a 100 to 1000 fold drop in estrogen levels in the first three days postpartum, which may elevate monoamine oxidase A (MAO-A). MAO-A metabolizes serotonin, norepinephrine and dopamine and MAO-A creates oxidation. Depletion of these neurochemicals is associated with sad mood.

There are two different models of mood disturbance in postpartum. The first model is postpartum blues for which the prevalence is approximately 85% and it increases the risk of PPD four fold. The greater the severity of postpartum blues the greater is the risk for developing PPD. Postpartum blues is a mild syndrome involving fatigue, insomnia, poor appetite, crying, anxiety and emotional lability. It is usually seen within days 4 to 6 postpartum, with the peak in day 5. Symptoms usually resolve within 10 days; however, some individuals continue to postpartum depression. The second model is excessive crying in the first 18 months postpartum, but not meeting clinical level symptoms of depression. A substantial proportion of women experience this second state and are at greater risk for clinical depression. Prevention strategies (referenced synonymously herein as "prophylaxis") used prior to onset of PPD may help both groups.

In this Example, the dietary supplement protocol used in Example 1, involving the two amino acids tryptophan and tyrosine, as well as blueberry juice/extract (representing a natural antioxidant) is used, and the effect on the intensity of postpartum blues is observed at day 5 postpartum. The protocol described herein was also used in women within the first 18 months postpartum who have crying spells.

Amino acid supplementation at the levels described in the instant protocol is shown to be safe for nursing mothers, on the basis of safe levels found in breast milk.

Many amino acids and most medications freely cross into breast milk. In contrast to medications, such crossing should not affect total concentrations of amino acids such as tryptophan and tyrosine into breast milk. The reason is that approximately 98% of tryptophan in breast milk is contained in proteins and peptides and that 99% of tyrosine in breast milk is contained in proteins and peptides. Different supplementation doses of oral tyrosine (0 g (none), 2, 5 or 10 grams) (n=6 each) or oral tryptophan (0 g (none), 2 or 4 grams) (n=6 each) were evaluated for resulting levels in breast milk. There was no change in total tryptophan levels in breast milk observed, despite changes in plasma tryptophan levels (data not shown). Similarly after oral dosing of tyrosine, there was no change in total tyrosine levels in breast milk, despite changes in plasma tyrosine levels (data not shown). The amount of free tyrosine and free tryptophan in breast milk did increase, but given that over 99% of these two amino acids are contained within proteins of fixed chains, their total levels did not change significantly in breast milk after oral supplementation. The percentage of free tryptophan and tyrosine found in breast milk following the oral supplementation described above were similar to levels found in many infant formulas (data not shown).

The doses selected for the instant supplementation protocol are 10 g tyrosine and 2 g tryptophan with regard to reducing the susceptibility to sad mood induction. Tyrosine supplement at the dose of 10 grams is selected, as based on the data described above, this dose did not significantly impact total tyrosine levels in breast milk, but was significantly increased in maternal plasma and was extremely well tolerated by subjects.

Tryptophan is supplemented at the dose of 2 grams, and based on clinical trial data noted above, this dose did not have any effects on total tryptophan levels in breast milk, was significantly increased in maternal plasma, and was extremely well tolerated by the subjects. Although the 4 gram level did not increase total tryptophan in breast milk either, but this level can be associated with nausea subjects receiving that dose.

Methods.

Healthy women recruited to the supplement or control (unsupplemented) group and assessed on their day 5 postpartum, after receiving the treatment protocol referred to herein as "TTB" for 2 g tryptophan, 10 g tyrosine and blueberry extract.

Subjects. The main inclusion criteria for subjects entering the study are as follows. The subject, as reported by them, is in a good health. The subject is not taking any medication. The subject is not taking any investigational medicinal product within 8 weeks. Other general medical requirements for inclusion: age 18 to 45; BMI 19 to 40 (kg/m$^2$); resting pulse between 45 and 100 bpm; systolic blood pressure between 91 and 139 mmHg (inclusive); diastolic blood pressure between 51 and 90 mmHg (inclusive); orthostatic blood pressure change <20 mmHg (based on the difference between supine and standing (1 minute) systolic blood pressure). General exclusion criteria for subjects are if the subject has been diagnosed with any axis 1 and 2 disorders based on Structured Clinical Interview (SCID) for DSM-IV interview; if the subject had a current diagnosis of bipolar disorder, substance abuse disorder, schizophrenia, or borderline personality disorders; if the subject has been smoking in the past 5 years.

Supplement sources. The dietary supplements are: tryptophan, tyrosine and blueberry extract. The tryptophan is delivered in the form of 1 g tablets, and 2 tablets are taken for a 2 gram dose. Tryptophan is obtained as L-tryptophan tablets from Apotex, Canada in containers containing 100 tablets. Tyrosine is obtained as L-Tyrosine capsules from Natural Factors (Coquitlam, Canada). Each container has 90 capsules of 500 milligram L-tyrosine capsules. The dose to be consumed by each subject is 10 grams, which is delivered with these capsules. The blueberry extract powder is supplied by VitaBlue™ and is purchased from FutureCeuticals, (Monence Ill., USA), and the amount used is about the equivalent to a 1-cup serving of blueberries. Blueberry juice is obtained locally from a commercial source.

Dosing Protocol. In day-5 postpartum women receiving the supplement, on the night of day 3 postpartum, the subject receives: blueberry juice+blueberry extract. On the morning of day 4 postpartum, the subject receives: blueberry juice+blueberry extract. On the night of day 4 postpartum the subject receives: Tryptophan tablets for 2 grams (2×1 g tablets) plus blueberry juice and blueberry extract.

The composition of the dietary supplement based on blueberry as an antioxidant source is outlined in Table 1 of Example 1 above. In a 355 g volume of fluid, a beverage component comprising blueberry juice was provided to the subjects for combination with a sachet of blueberry extract powder. The composition is estimated to comprise about 180 kCal per dose, calculated on the basis of carbohydrate content.

On the morning of day 5 postpartum, the subject consumes tyrosine capsules for 10 grams tyrosine, as well as blueberry juice+blueberry extract.

This study involves 2 visits per subject: screening and the main study day. The first screening involves SCID for DSM-IV; BDI, DAS and NEO-PR, as well as a urine drug screen. The second visit schedule is shown in Table 4. Optionally, there are two follow-up phone calls (one call 1 month after the second visit and one call 3 months after the second visit).

TABLE 4

Schedule for Protocol (Main Study Day is Day-5 Postpartum)

| Day Postpartum | Time | Activity |
|---|---|---|
| Day 3 | 9:00 pm | Blueberry Drink Intake (blueberry extract + blueberry juice) or none (control) |
| Day 4 | 10 am | Blueberry Drink Intake (blueberry extract + blueberry juice) or none (control) |
| Day 5 Study Day | 8:40 am | Tyrosine & Blueberry Drink Intake (blueberry extract + blueberry juice) or none (control) |
| | 9:40 am | Stein Blue Scale |
| | 9:50 am | Neutral mood induction procedure |
| | 10:10-10:15 | VAS |
| | 10:15-10:30 | DAS |
| | 10:30-10:50 | POMS |
| | 10:50-10:55 | VAS |
| | 10:55-11 | Break |
| | 11-11:20 | Sad mood induction procedure |
| | 11:20-11:25 | VAS |
| | 11:25-11:40 | DAS |
| | 11:40-12 | POMS |
| | 12-12:05 | VAS |
| | 12:05-12:10 | Break |
| | 12:10-12:45 | Emotional Stroop Test |
| | 12:45-12:50 | VAS |
| | 12:50-1:00 | Break |
| | 1:00-1:15 | Neutral mood induction procedure |
| | 1:15-1:20 | VAS |
| | 1:20-1:30 | BDI |
| | 1:30-1:40 | Edinburgh Postnatal Scale |

Abbreviations:
MIP = Mood Induction Procedure,
VAS = Visual Analog Scale,
POMS = Profile of Mood State,
DAS = Dysfunctional Attitude Scale,
BDI = Beck Depression Inventory Scale Sad mood induction is done based on the Velten Mood Induction Procedure, together with music, as described below. The Velten Procedure is a widely used technique for studying affective influences upon behavior has demonstrated effectiveness in altering subjective emotional states. Velten mood induction procedure is a series of 60 self-referent statements. Negative statements reflected pessimism, dissatisfaction, and lethargy; for example "life is a heavy burden". Neutral statements example are such as "an orange is a citrus fruit". Subjects are asked to read each statement, printed individually, first to themselves and then aloud, and to 'feel and experience each statement as it would apply to you personally'. Subjects are left alone in the room during the mood induction procedure.

To further facilitate the sad MIP, participants are also presented with a piece of music, on headphones, that conveys the tone of the mood trying to be induced. For sad MIP, subjects listen to Prokofiev's "Russia Under the Mongolian Yoke". For neutral MIP, Mozart's "Piano Concerto No. 21 in C Major" is played. Clinical rating measures of mood and symptoms of depression are assessed before and after MIP.

The first visit is a screening visit. On this day subjects will be evaluated for general health status through a standardized health questionnaire. SCID DSM-IV, Beck Depression Inventor Scale (BDI) and Dysfunctional Attitude Scale (DAS) and The Revised NEO Personality Inventory (NEO PI-R) are filled out. A urine test is done in order to screen for any drug use.

SCID I and II are applied for each subject. This is a diagnostic exam used to determine DSM-IV Axis I disorders (major mental disorders) and Axis II disorders (personality disorders).

BDI is the most widely used and validated self-report test, which measures the existence and severity of clinical depression symptoms.

DAS is a 40-item instrument that is designed to identify and measure cognitive distortions, particularly distortions that may relate to or cause depression. Form A and form B of the DAS is administered in a counterbalanced design between subjects.

NEO PI-R is recognized internationally as a gold standard for personality assessments and is a measure of the five major domains of personality including: Extraversion, Agreeableness, Conscientiousness, Neuroticism, and Openness to Experience; as well as the six facets that define each domain.

The second visit would be the main study day on day 5 postpartum. The timing of each test done during this visit is shown in Table 4. For each supplement that is taken prior to the second visit, subjects receive a reminder phone call.

After subjects arrive for testing on Day 5, and complete the Stein Blue Scale is a self-rated scale and consists of 13 symptoms (depression, crying, anxiety, tension, restlessness, exhaustion, dreaming, appetite, headache, irritability, poor concentration, forgetfulness and confusion). Subjects then go through a neutral mood induction based on the Velten Mood Induction Procedure. To facilitate the neutral MIP, participants listen to a piece of neutral music. Following the neutral MIP, subjects fill out the following questionnaires in the stated order: VAS, DAS POMS, VAS;

VAS uses a 10-point scale for participants to indicate the extent to which each of the 8 items is consistent with how they feel in the moment. The items included depressed, happy, restless, sad, anxious, angry, drowsy and alert. Within VAS, mood assessment is done first. DAS is then conducted.

POMS contains of 65 adjectives rated by participants on a 5-point scale. Six factors are derived that include tension, depression, anger, fatigue, vigor and confusion 104.

VAS is then conducted followed by a break.

Subjects then go through a sad mood induction based on the Velten Mood Induction Procedure. To facilitate the sad MIP, participants are then presented with a piece of sad music. Following the sad MIP, subjects will repeat the following questionnaires in the stated order: VAS; DAS; POMS; VAS.

After the completion of the above questionnaires, subjects go through an Emotional Stroop Test. This test is used as an information-processing approach to assess emotions. The emotional Stroop test examines the response time of the participant to name colors of negative emotional words.

Subsequently, subjects go through a neural mood induction, followed by VAS, and BDI. Subjects participating on day 5 postpartum have the choice to either come to Centre for Addiction and Mental Health (Toronto, Canada) for their second visit or have a visit at their house.

Follow-up phone calls are placed, and involve general questions regarding the subject's mood and feeling over the past few weeks and will also involve completing the questionnaires SCID for DSM-IV, Edinburgh Postnatal Scale and BDI.

Statistical Analysis. The primary outcome is the use of repeated measures analysis of variance with the visual analogue scale (VAS) of depressed mood as the repeated measure, with the TTB treatment versus no supplement as the between subject measure. A secondary outcome may be expressed as a change in profile of mood state (POMS) scale, using repeated measures analysis of variance with the POMS score as the repeated measure and TTB treatment versus no supplement as the between subject measure.

A further outcome may be evaluated as change in Dysfunctional Attitude Scale (DAS), using repeated measures analysis of variance with the DAS score as the repeated measure and TTB versus no supplement as the between subject measure. ANOVA may be used to compare the results between the groups.

Safety and tolerability of treatment on the subjects is evaluated.

Results.

Figure 4A:
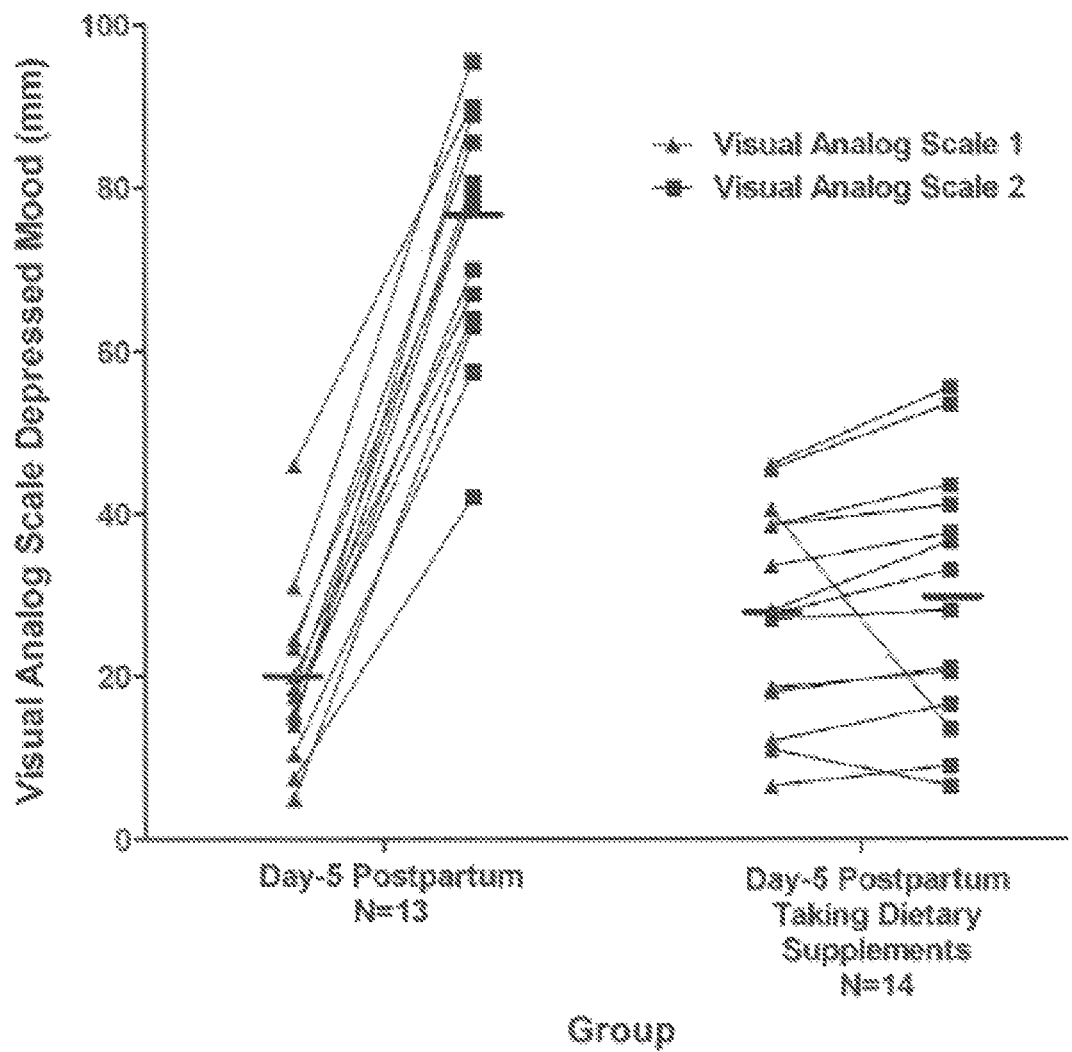
FIG. 4A is a chart showing visual analog scale depressed mood values for day-5 postpartum subjects with or without the supplementation protocol, illustrating a greater resilience to depressed mood induction with the supplement.

FIG. 4A shows that subjects at Day-5 postpartum treated with the TTB protocol described herein showed greater resilience to depressed mood induction. A visual analog scale illustrating depressed mood values at day-5 in postpartum subjects is shown for subjects with or without the supplementation protocol. For each subject, a triangle data point indicates initial mood score, while a square data point indicates mood score following depressed mood induction, and the subject's scores are connected with a line. Without the supplementation with the treatment protocol, score increased consistently (N=13) at day-5 postpartum. However, following the treatment protocol described herein, with day-3, day-4 and day-5 postpartum supplementation according to the Schedule of Table 4, subjects in the treatment group (N=14) showed a greater resilience to depressed mood induction, as they did not have a significantly increased score with the supplement.

Average visual analog scale depressed mood score for the untreated group before and after mood induction was about 20 mm versus about 75 mm, demonstrating about a 3.7-fold change in the score. However, in the treatment group, the subjects' initial scores averaged about 27 mm (not significantly different from the initial scores of the untreated group, and increased to about 30 mm, (representing a non-significant change), demonstrating a significantly lower post-induction score than the untreated group and greater resilience to sad mood induction. The analysis of variance in these data showed a statistically significant group effect on change in VAS depressed mood scores ($F (1, 25)=191.86$, $p<0.001$).

Figure 4B:
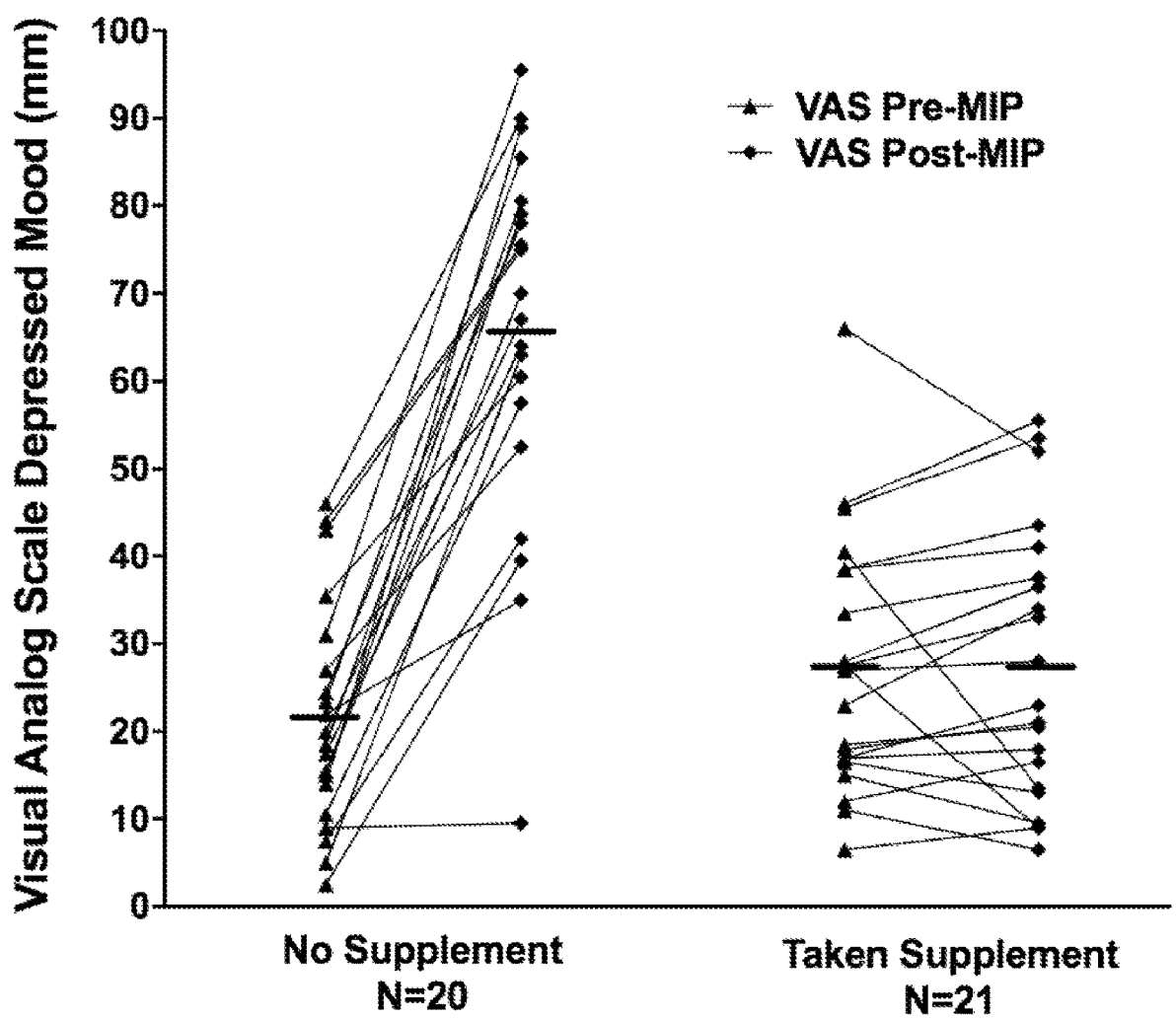
FIG. 4B shows visual analog scale depressed mood evaluation for women within the 5-day postpartum period following either no supplementation (n=20) or following supplementation (n=21) with a regime as described herein, showing a larger sample size of subjects than in FIG. 4A following additional subject enrollment. Confirming the data of FIG. 4A, a greater incidence of depressed mood occurred as a result of the post-mood induction protocol for unsupplemented subjects.

FIG. 4B shows a chart similar to FIG. 4A, but after more subjects were enrolled in the study. The numbers confirm the data, and emphasize the trend of FIG. 4A. The larger sample size permits additional comparison of the change in visual analogue scale after depressed mood induction in subjects within the 5-day postpartum period. In the larger data groups shown in FIG. 4B (within which, subjects from FIG. 4A are included), it was observed that unsupplemented (N=20) subjects versus supplemented (N=21) subjects exhibited a higher susceptibility to depressed mood induction, consistent with the data in FIG. 4A. The change between VAS 1 (Pre-MIP) to VAS 2 (POST-MIP) represents the change in reported mood on a measurable scale after undergoing the depressed mood induction protocol (MIP), as outlined in the protocol of Example 1. A highly significant and pronounced effect is confirmed with the larger number of subjects in the study groups. In FIG. 4B, VAS scores changed from 21 to 65 mm in unsupplemented group from pre- to post-MIP, as compared with no detectable change between VAS changing from 26 to 27 mm for pre- to post-MIP in the supplemented group. Univariate analysis of variance showed a strong and significant group effect on change in VAS mood scores ($F(1,14)=21.904$, $p<0.005$).

Example 3

Evaluating Impact of a Standard Serving on a Body Weight Basis

Subjects and protocols are as described above in Example 2.

The change in Visual Analog Scale Depressed Mood on a dose per body weight basis is evaluated in the subjects in the treatment group receiving TTB as described in Example 2. This analysis was conducted to evaluate whether the TTB treatment is appropriately given as a standard serving size basis regardless of subject body weight, or if dose on a body weight basis is more correlative to outcome. It was shown that no correlation exists between body weight and change in VAS depressed mood when a standard serving size was used for all subjects. These data reveal that a standardized serving of TTB can be provided to subjects regardless of body weight before pregnancy or body weight during pregnancy.

Figure 5:
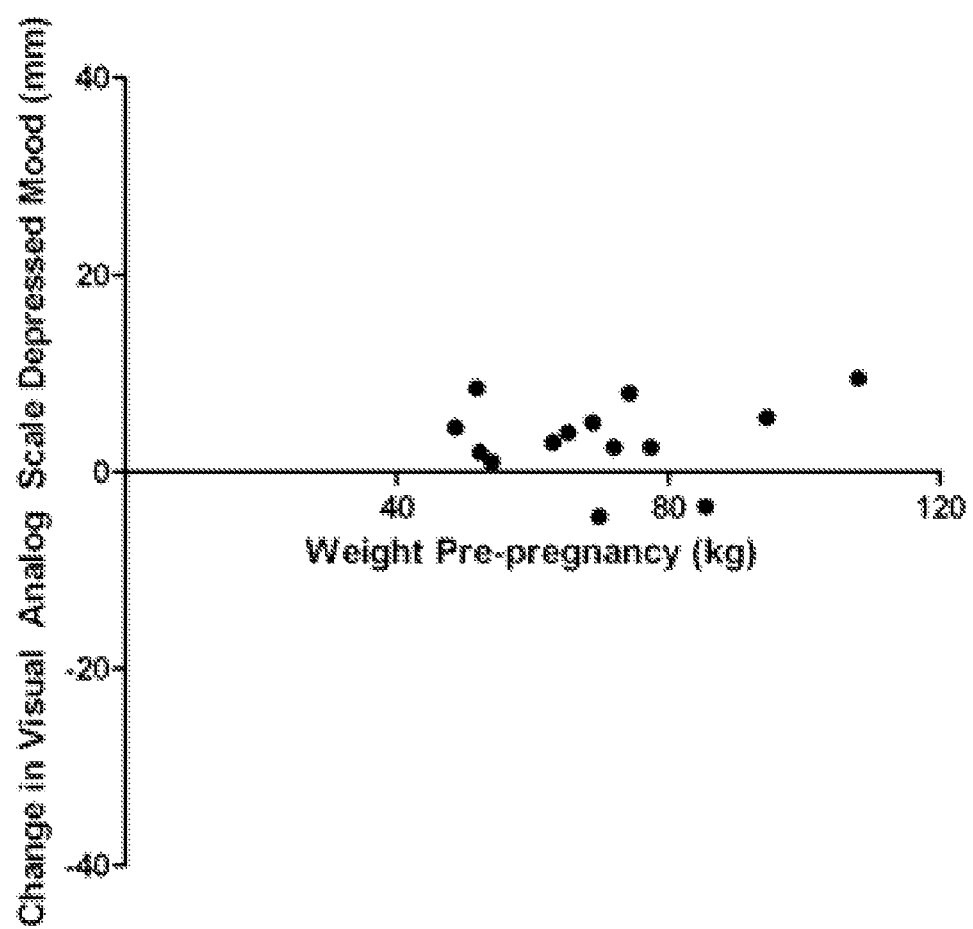
FIG. 5 is a chart showing that there is no significant correlation between weight before pregnancy (kg) and the change in visual analog scale depressed mood scores in subjects treated with TTB in Example 3.

FIG. 5 reports change in Visual Analog Sale Depressed Mood scores before and after depressed mood induction on day-5 postpartum for those individuals treated with TTB as described in Example 2, and graphs this against body weight of the subject before pregnancy. There is no significant correlation. This affirms that lighter subjects do not have a greater change in score upon consuming the same serving size as heavier subjects even though the amount of TTB treatment consumed per unit body weight is necessarily greater. Given that there is no significant correlation between weight before pregnancy (kg) and the change in visual analog scale depressed mood scores in subjects before and after being treated with a common serving size of TTB, it suggests that a standardized serving size for the TTB treatment, regardless of a subject's body weight is appropriate.

Figure 6:
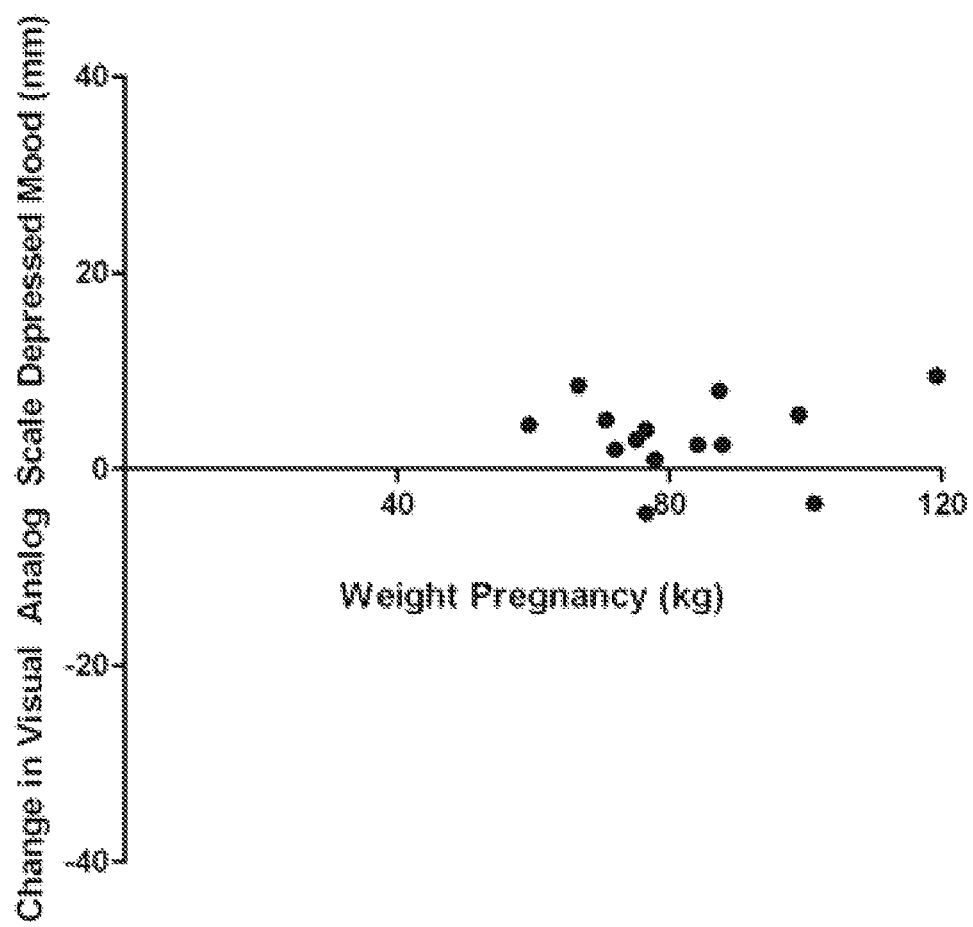
FIG. 6 is a chart showing that there is no significant correlation between weight during pregnancy (kg) and the change in visual analog scale depressed mood scores in subjects treated with TTB in Example 3.

FIG. 6 reports change in Visual Analog Sale Depressed Mood scores before and after depressed mood induction on day-5 postpartum for those individuals treated with TTB as described in Example 2, and graphs this against body weight of the subject during pregnancy. Similar to FIG. 5, there is no correlation between change in mood and body weight during pregnancy, upon consumption of a standard treatment serving size for these subjects at day-5 postpartum. These data also suggest that a standard treatment serving size is appropriate regardless of a subject's body weight during pregnancy.

Example 4

Supplemented Subjects Show Greater Resilience to Depressed Mood Induction within 18 Months Postpartum In this Example, the study protocol used is similar to that described above in Example 3, with the following changes or clarifications. The subjects were a group of postpartum women who experienced postpartum crying within 18 months postpartum, and who complained of tearful episodes but were not deemed to meet the criteria for a full major depressive episode. This group, referenced herein as the postpartum criers group, represents another type of mood syndrome sometimes observed in postpartum.

Dietary supplementation with tryptophan, tyrosine and blueberry extract, was undertaken in a manner similar to the supplementation outlined in Example 3. Supplements were given to the subjects in the supplementation study group, and no supplement was given to the control group. It was evaluated whether supplementation would reduce sadness after a sad mood induction protocol (undertaken as described in Example 3). Healthy women were included in the study, who were in their first 18 months postpartum and who were experiencing crying spells but who did not meet the criteria for major depressive disorder. These subjects received a supplement of 2 g tryptophan, 10 g tyrosine and then a blueberry extract in a juice mixture, as outlined in Example 3, in a regimen referred to as "TTB".

The specific 3-day protocol involved delivering to the supplemented women: night of day 1: blueberry juice+blueberry extract; morning of day 2: blueberry juice+blueberry extract; night of day 2: tryptophan tablets for 2 grams+blueberry juice+blueberry extract; and morning of day 3 (main study day): tyrosine capsules for 10 grams+blueberry juice+blueberry extract. On day 3, mood induction was undertaken as described above in Example 3.

Figure 7:
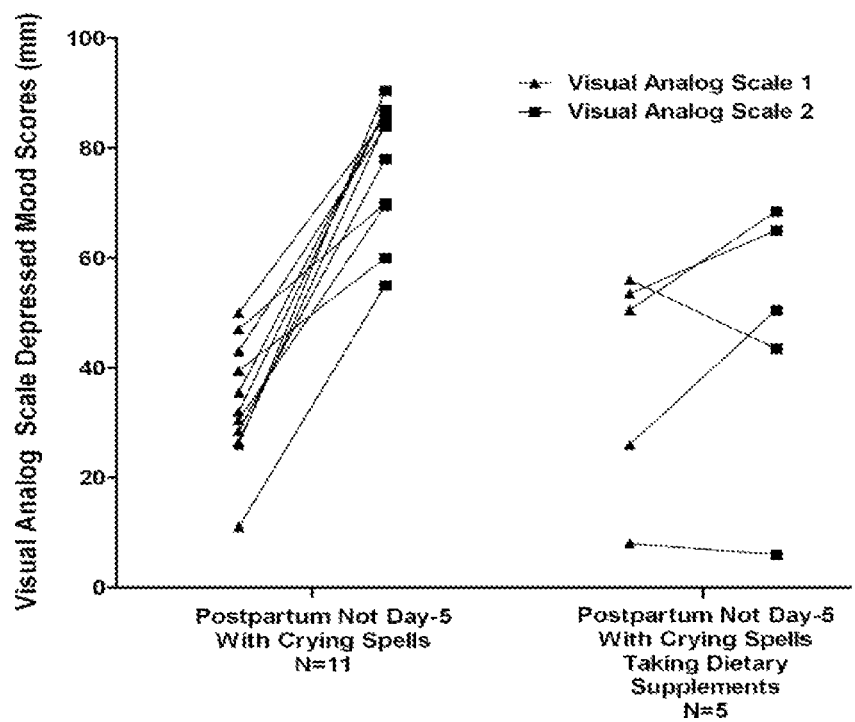
FIG. 7 is a chart showing visual analog scale depressed mood values for criers within 18 month postpartum with or without the supplementation protocol, illustrating a greater resilience to depressed mood induction with the supplement over a 3-day protocol described in Example 4.

FIG. 7 shows the effect of mood induction on subjects susceptible to crying spells who are within 18 months postpartum, but past day 5. Unsupplemented subjects (n=11) are consistently effected by an increase in depressed mood score, while supplemented subjects (n=5) illustrate resilience to depressed mood, with no consistent change in depressed mood score.

Table 5 shows information pertaining to the subjects described herein, for which VAS data is provided in FIG. 7. Criers were defined as women within 18 months of giving birth that reported crying spells but who did not have a major depressive episode (MDE) after giving birth.

Age, time since giving birth, a Stein Blues Scale Value, Beck Depression Inventory Scale (BDI) screening (a measure of severity of depressive symptoms), and Edinburgh Postnatal Depression Scale (EPDS) value are shown. EPDS is a set of 10 screening questions testing for symptoms that are common in women with depression and anxiety during pregnancy and in the year following the birth of a child. EDPS is used as a measure that, when elevated, indicates a higher likelihood of developing postpartum depression. While data in Table 5 shows various indices pertaining to depressed mood or postpartum depression, the data is not presented here to illustrate post-supplementation results, but rather to indicate that the two groups of criers (those designated to the supplementation group versus the control group) were appropriate groups for comparison, with similar initial profiles.

TABLE 5

| | Characteristics of Criers | | | | |
|---|---|---|---|---|---|
| | Age | Time since birth (mo) | Steins Blues Scale | BDI screening | EPDS |
| Criers taking dietary supplement | | | | | |
| 1 | 35 | 16 | 8 | 27 | 10 |
| 2 | 34 | 6 | 3 | 20 | 11 |
| 3 | 27 | 1 | 1 | 16 | 2 |
| 4 | 37 | 4 | 5 | 19 | 14 |
| 5 | 30 | 9 | 4 | 5 | 10 |
| Criers not taking supplement | | | | | |
| 1 | 30 | 12 | 10 | 7 | 13 |
| 2 | 33 | 3 | 13 | 14 | 11 |
| 3 | 26 | 15 | 7 | 22 | 8 |
| 4 | 23 | 2 | 6 | 27 | 18 |
| 5 | 22 | 7 | 15 | 32 | 20 |
| 6 | 32 | 6 | 0 | 5 | 5 |
| 7 | 28 | 0.75 | 11 | 20 | 16 |
| 8 | 28 | 12 | 6 | 28 | 15 |
| 9 | 35 | 2 | 6 | 12 | 5 |
| 10 | 33 | 14 | 10 | 25 | 11 |
| 11 | 30 | 3 | 12 | 18 | 18 |
| Mean ± SD | 30.18 ± 4.34 | 7.04 ± 5.26 | 7.31 ± 4.28 | 18.56 ± 8.33 | 11.69 ± 5.09 |

Figure 8:
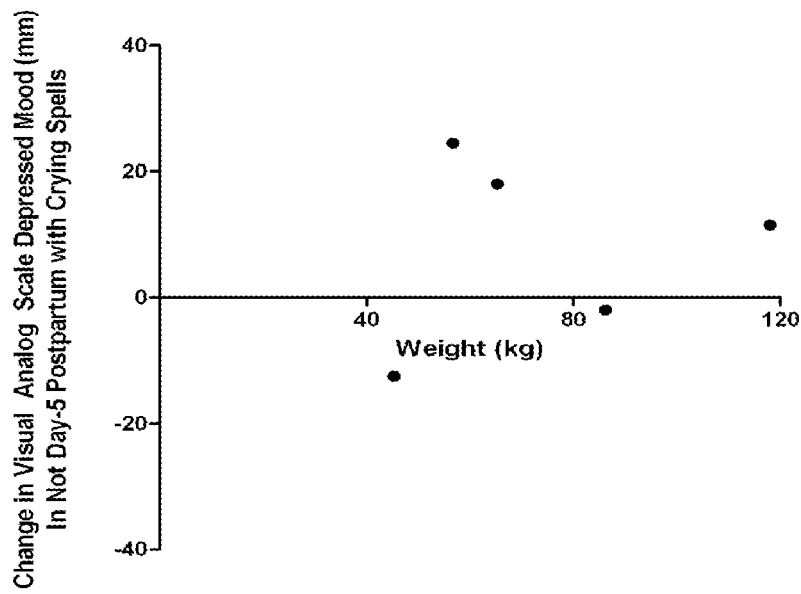
FIG. 8 is a chart showing that there is no significant correlation between weight before pregnancy (kg) and the change in visual analog scale depressed mood scores in subjects treated with TTB supplementation in Example 4.

BDI: Beck Depression Inventory Scale;
EPDS: Edinburgh Postnatal Depression Scale FIG. 8 shows that the effect of supplementation in the 5 subjects tested is independent of weight of the subject, which is consistent with findings described in Example 3. Thus, the serving size selected in this example had an effect on subjects that was independent of body weight.

These data illustrate the effect of the supplement on the women who complain of crying and are within 18 months postpartum, and as such, are beyond the day 5 group in the postpartum period. Thus, supplementation with the regimen of tryptophan, tyrosine and blueberry extract/juice reduces susceptibility to experiencing a sad mood in subjects outside of the day-5 postpartum period and up to 18 months postpartum who experience crying but do not meet criteria for a full major depressive episode. These data also indicate that such subjects may benefit from use of the described method not only at day-5 postpartum, but on a periodic or repeated basis when crying episodes occur.

Example 5

Follow-Up Assessment of Effect of Supplementation on Incidence of Postpartum Depression within One Year Postpartum Follow-up was conducted with subjects who had participated in the study outlined in Example 2. The subjects were either contacted or came to Centre for Addiction and Mental Health (Toronto, Canada) for a subsequent visit on, or after, 1 year postpartum. Subjects were questioned about occurrence of postpartum depression within the first postpartum year. The subjects had either taken the supplemental regimen in the 5-day postpartum period, or had not taken the supplement in this period. In total, 38 subjects were followed-up, including 17 who had not been supplemented, and 21 subject who had been supplemented at about day 5 postpartum.

Of the 17 subjects followed up with from the unsupplemented group, two subjects reported having had an incident of postpartum depression (PPD), which represents 12% of the unsupplemented subjects participating in follow-up.

Of 21 subjects followed up with from the supplemented group, only one subject reported postpartum depression within the first postpartum year, which represents 5% of the supplemented subjects participating in follow-up.

A typical rate of postpartum depression occurrence within the first postpartum year is about 13%. This is consistent with the unsupplemented group that showed a 12% PPD occurrence, within the postpartum year. However, the supplemented group exhibited a lower incidence of PPD, suggesting a protective effect of the supplement when utilized according to the regimen described herein at the early stages. Preventative or prophylactic use of the supplement according to the described regimen can influence and reduce occurrence of PPD events in the first year postpartum.

The described method exhibited a marked influence of treatment or prophylaxis of postpartum blues, sad mood, and depressed mood at the early stages (for example at around day 5 postpartum), on later development of postpartum depression within the 1-year postpartum period. Treatment of the blues or crying spells early-on could help prevent later and more severe PPD. Blues and sadness following the birth of a baby is a risk factor for postpartum depression, which the treatment regime can help to remedy, whether or not individuals experience depressed mood at or around day 5 postpartum.

Example 6

Anthocyanin Content of Fruits, Vegetables, Nuts, Legumes, and Juices or Extracts Thereof.

Antioxidant sources may be derived from many foods and their extracts or isolates. These foods include fruits, vegetables, nuts, legumes, and juices or extracts of these. While antioxidant content of a certain food or extract can be evaluated on the basis of ORAC values, the food or extract sources eligible for use in the current method or regimen also have the property of being anthocyanin-containing. While anthocyanins are known to be antioxidants, there are other components of plant-derived foods that exhibit antioxidant effects.

On the basis of data published by Wu et al., 2006, high levels of anthocyanins, such as found in water-soluble plant pigments, have been estimated in a number of readily available plant sources. These compounds are in part responsible for the blue, purple, and red colors of plant tissues. Over 600 types of naturally occurring anthocyanins have been reported in a wide variety of foods. Wu et al., 2006, assessed 6 different anthocyanins in readily available plant foods, as well as total anthocyanin content.

Table 6 shows exemplary foods found to be high in total anthocyanin on a fresh-weight basis, together with the total anthocyanin content.

TABLE 6

Anthocyanin content of High-Anthocyanin Foods (Wu et al., 2006)

| Food | Total Anthocyanin content (mg/100 g) |
| --- | --- |
| Red Delicious Apples | 12 |
| Blackberry | 245 |
| Blueberry - Cultivated | 390 |
| Blueberry - Wild | 490 |
| Cherry | 120 |
| Chokeberry | 1480 |
| Cranberry | 140 |
| Black Currant | 475 |
| Red Currant | 12 |
| Elderberry | 1375 |
| Gooseberry | 14 |
| Red Grape | 27 |
| Concord Grape | 120 |
| Nectarine | 7 |
| Peach | 5 |
| Black Plum | 124 |
| Raspberry | 92 |
| Strawberry | 21 |
| Eggplant | 85 |
| Red Cabbage | 322 |
| Red onion | 50 |
| Red Radish | 100 |
| Pistachio Nuts | 7.5 |
| Black Bean | 45 |
| Grape Juice | 14 |
| Wine | 11 |

Juices and/or extracts may be made, for example from fruits such as: apples, blackberry, blueberry (cultivated or wild), cherry, chokeberry, cranberry, black currant, red currant, elderberry, gooseberry, red grape, concord grape, nectarine, peach, black plum, raspberry, strawberry, melon, pineapple, or pomegranate. Further, juices and/or extracts may be made from eggplant, red cabbage, red onion, red radish, *Brassica oleracea* plants such as cabbage, broccoli, cauliflower, kale, Brussels sprouts, savoy, or Chinese kale; peppers, plant oils. Additionally, antioxidant sources may include juices and extracts high in anthocyanins from such sources as lentils and black beans, plant oils, and tree nuts such as pistachios may be used.

While the list provided here is not exhaustive, the different anthocyanin-containing foods, juices or extracts which may be used in the methods described herein are understood to be readily available and easy to make by those of skill in the art, in order to prepare the antioxidant source for use in the treatment regime. A skilled person can readily formulate an antioxidant source for use in the described regimen, which would meet the stated ORAC value criteria and contain anthocyanins. An antioxidant source may comprise anthocyanins at levels of at least about 5 mg/100 g, such as at least about 10 mg/100 g or more could be used in the regime described herein. For example, a food, extract or juice having at least about 20 mg/100 g, 50 mg/100 g, 75 mg/100 g, 100 mg/100 g, 150 mg/100 g, 200 mg/100 g, 150 mg/100 g, 200 mg/100 g; 300 mg/100 g; 400 mg/100 g or more could be used in the described regimen. The dose may range from 5 to 1000 mg of anthocyanin in the individual doses of antioxidant source, such as from 10 to 1000, from 20 to 800 mg, or from 50 to 750 mg. This amount of anthocyanin may be obtained from the antioxidant source food, its extract or juice, or from an isolated anthocyanin.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

All references are herein incorporated by reference.

Clark D M, The Velten Mood Induction Procedure and cognitive models of depression: a reply to Riskind and Rholes Behav. Res. Ther. 1985; 23:667-669.

Dowlati Y et al., Effect of dysfunctional attitudes and postpartum state on vulnerability to depressed mood. J Affect Disord 2014 June; 161:16-20.

Gorbach S L, U.S. Pat. No. 6,083,526, issued Jul. 4, 2000.

Haytowitz et al., USDA Database for the Oxygen Radical Absorbance Capacity (ORAC) of Selected Foods, Release 2, U.S. Department of Agriculture, Agricultural Research Service. May 2010 (1-46).

Meyer J H et al., Elevated monoamine oxidase a levels in the brain: an explanation for the monoamine imbalance of major depression. Arch Gen Psychiatry 2006 November; 63(11):1209-16.

Meyer J H et al., Brain monoamine oxidase A binding in major depressive disorder: relationship to selective serotonin reuptake inhibitor treatment, recovery, and recurrence. Arch Gen Psychiatry 2009 December; 66(12): 1304-12.

O'Hara M W et al. Prospective study of postpartum blues. Biologic and psychosocial factors. Arch Gen Psychiatry. 1991 September; 48(9):801-6.

O'Hara M W et al, Rates and risk of postpartum depression: a meta-analysis. Int Rev Psychiatry 1996: 8(1):37-54.

Prior R L et al. Assays for hydrophilic and lipophilic antioxidant capacity (oxygen radical absorbance capacity (ORACFL)) of plasma and other biological and food samples. J. Agric. Food Chem., 2003, 51:3273-3279.

Rekkas P V et al., Greater Monoamine Oxidase A Binding in Perimenopausal Age as Measured With Carbon 11-Labeled Harmine Positron Emission Tomography, JAMA Psychiatry Jun. 4, 2014; doi:10.1001/jamapsychiatry.2014.250.

Sacher J et al., Elevated brain monoamine oxidase A binding in the early postpartum period. Arch Gen Psychiatry 2010 May; 67(5):468-74.

Smith L J et al., Effects of ovarian steroids and raloxifene on proteins that synthesize, transport, and degrade serotonin in the raphe region of macaques. Neuropsychopharmacology 2004 November; 29(11): 2035-2045.

Sullivan M G, Tryptophan, Tyrosine May Battle Early Postpartum Depression. Clinical Psychiatry News 2011 Mar. 18; 1-3.

Velten E., A laboratory task for induction of mood states. Behav. Res. Ther. 1968; 6:473-482.

Wu et al., Concentrations of Anthocyanins in Common Foods in the United States and Estimation of Normal Consumption. J. Agric. Food Chem. 2006; 54: 4069-4075.

The invention claimed is:

1. A method for treating or prophylaxis of postpartum blues or depression comprising administering to a subject in need thereof:
   an antioxidant source;
   a tryptophan composition comprising from 1.0 g to 5.0 g of tryptophan; and
   a tyrosine composition comprising from 2.0 g to 50 g of tyrosine.

2. The method of claim 1, wherein the antioxidant source comprises a food.

3. The method of claim 1, wherein the antioxidant source comprises a composition comprising a plant extract and an acceptable diluent.

4. The method of claim 1, wherein the antioxidant source comprises:
   grapes, berries, citrus fruit, pomegranate, tomato, squash, carrot, sweet potato, a dark green vegetable, a beet, a leafy vegetable, a *Brassica oleracea* vegetable, a pepper, a melon, pineapple, lentils, a plant oil, and/or a tree nut; and/or a juice, extract, or isolated antioxidant compound therefrom.

5. The method of claim 1, wherein the antioxidant source comprises blueberries, blueberry juice, blueberry extract, and/or an anthocyanin isolated from blueberry.

6. The method of claim 1, wherein the antioxidant source comprises an anthocyanin.

7. The method of claim 1, wherein the antioxidant source has an ORAC value at least about 3000 µmol TE/serving.

8. The method of claim 1, wherein the antioxidant source has an ORAC value of at least about 5000 µmol TE/serving.

9. The method of claim 1, wherein the antioxidant source comprises a vitamin or micronutrient.

10. The method of claim 4, wherein the antioxidant source comprises a plant oil high in vitamin E.

11. The method of claim 1, wherein the antioxidant source comprises a precursor compound that is converted to an antioxidant form by the body after administration.

12. The method of claim 11, wherein the precursor compound comprises cysteine.

13. The method of claim 1, wherein the tryptophan composition comprises L-tryptophan in free amino acid form or in a peptide form, and an acceptable diluent.

14. The method of claim 1, wherein the tyrosine composition comprises L-tyrosine in amino acid form and an acceptable diluent.

15. The method of claim 1, wherein the tryptophan composition is administered on day-4 and the tyrosine composition is administered on day-5 postpartum.

16. The method of claim 1, wherein the antioxidant source is administered on more than one day from day-1 to day-5 postpartum.

17. The method of claim 16, wherein the antioxidant source is administered on day-3, day-4, and day-5 postpartum.

18. The method of claim 1, wherein the antioxidant source is additionally administered for 1-7 days following administration of the tryptophan composition.

19. The method of claim 1, wherein the antioxidant source is administered twice daily.

20. The method of claim 1, said method comprising administering the antioxidant source to the subject for at least 2 to 5 treatment days.

21. The method of claim 20, said method comprising administering the tryptophan composition on the evening of the penultimate treatment day, simultaneously or following the administration of the antioxidant source; and administering the tyrosine composition on the final treatment day.

22. The method of claim 21, wherein:
   the tryptophan composition comprises 2 g of tryptophan; and/or
   the tyrosine composition comprises 10 g of tyrosine.

23. The method of claim 1, wherein:
   the tryptophan composition consists of about 2 g of tryptophan;
   the tyrosine composition consists of about 10 g of tyrosine; and
   the antioxidant source has an ORAC value of at least about 5000 µmol TE/serving, and comprises blueberries, blueberry juice and/or blueberry extract.

24. The method of claim 1, wherein the tryptophan composition, the tyrosine composition, and/or the antioxidant source is in the form of a pill, a capsule, a tablet, a gel, a concentrate, a syrup, a bar, a cereal, a beverage, a shake, a powder, or a baked product.

25. The method of claim 1 wherein:
   at least one serving of the antioxidant source is administered on at least day-1 of a postpartum treatment regime of from 3 to 5 days; wherein the antioxidant source comprises an anthocyanin-containing fruit, vegetable, nut, legume, or a juice or extract thereof, and has an ORAC value of at least about 3000 µmol TE/serving;
   a serving of the tryptophan composition is administered simultaneously or following the antioxidant source on the penultimate day of the postpartum treatment regime, wherein the tryptophan composition comprises from 1.0 g to 5.0 g of tryptophan per serving in free amino acid form, and an acceptable diluent;
   a serving of the tyrosine composition is administered on the final day of the postpartum treatment regime, wherein the tyrosine composition comprises from 2.0 g to 50 g of tyrosine per serving in free amino acid form, and an acceptable diluent.

* * * * *